(12) United States Patent
Nishii et al.

(10) Patent No.: US 6,923,769 B2
(45) Date of Patent: Aug. 2, 2005

(54) METHOD AND APPARATUS FOR MONITORING BIOLOGICAL ABNORMALITY AND BLOOD PRESSURE

(75) Inventors: Katsuyoshi Nishii, Okazaki (JP); Teiyuu Kimura, Nagoya (JP); Satoshi Takeuchi, Nagoya (JP); Shinji Nanba, Kariya (JP); Junichiro Hayano, 5-33 Arata-cho, Showa-ku, Nagoya-city, Aichi-pref., 466-0844 (JP)

(73) Assignees: Denso Corporation, Kariya (JP); Junichiro Hayano, Aichi-pref. (JP)

( * ) Notice: Subject to any disclaimer, the term of this patent is extended or adjusted under 35 U.S.C. 154(b) by 415 days.

(21) Appl. No.: 10/151,251

(22) Filed: May 21, 2002

(65) Prior Publication Data
US 2002/0183627 A1 Dec. 5, 2002

(30) Foreign Application Priority Data

May 31, 2001 (JP) .................................... 2001-165297
Jan. 31, 2002 (JP) .................................... 2002-024056

(51) Int. Cl.⁷ .............................................. A61B 5/00
(52) U.S. Cl. ...................... 600/485; 600/500; 600/504
(58) Field of Search ........................ 600/485, 500–503, 600/504–507

(56) References Cited

U.S. PATENT DOCUMENTS

| | | | | |
|---|---|---|---|---|
| 5,255,686 A | | 10/1993 | Takeda et al. | |
| 5,485,848 A | * | 1/1996 | Jackson et al. | 600/485 |
| 5,533,511 A | * | 7/1996 | Kaspari et al. | 600/485 |
| 5,626,141 A | * | 5/1997 | Takeda | 600/490 |
| 5,879,307 A | | 3/1999 | Chio et al. | |
| 6,045,509 A | * | 4/2000 | Caro et al. | 600/481 |
| 6,176,832 B1 | * | 1/2001 | Habu et al. | 600/485 |
| 6,190,325 B1 | | 2/2001 | Narimatsu | |
| 6,280,390 B1 | * | 8/2001 | Akselrod et al. | 600/485 |
| 6,554,774 B1 | * | 4/2003 | Miele | 600/504 |

FOREIGN PATENT DOCUMENTS

JP          A-64-27534          1/1989

* cited by examiner

*Primary Examiner*—Robert L. Nasser
(74) *Attorney, Agent, or Firm*—Posz Law Group, PLC

(57) ABSTRACT

In a clinical and physiological abnormality monitoring apparatus, and blood pressure monitoring apparatus detects a blood pressure abnormality and the like of a body by employing a pulse wave signal. A frequency analysis is carried out with respect to a pulse wave signal, while this pulse wave signal corresponds to time sequential data of pulse waves. As a result, both a C-frequency component indicative of a fluctuation component of a base line of the pulse wave signal, and also an A-frequency component representative of the respective pulse waves are acquired. A ratio C/A of power of a peak contained in the C-frequency component with respect to power of a peak contained in the A-frequency component is calculated to determine abnormality of the blood pressure.

45 Claims, 18 Drawing Sheets

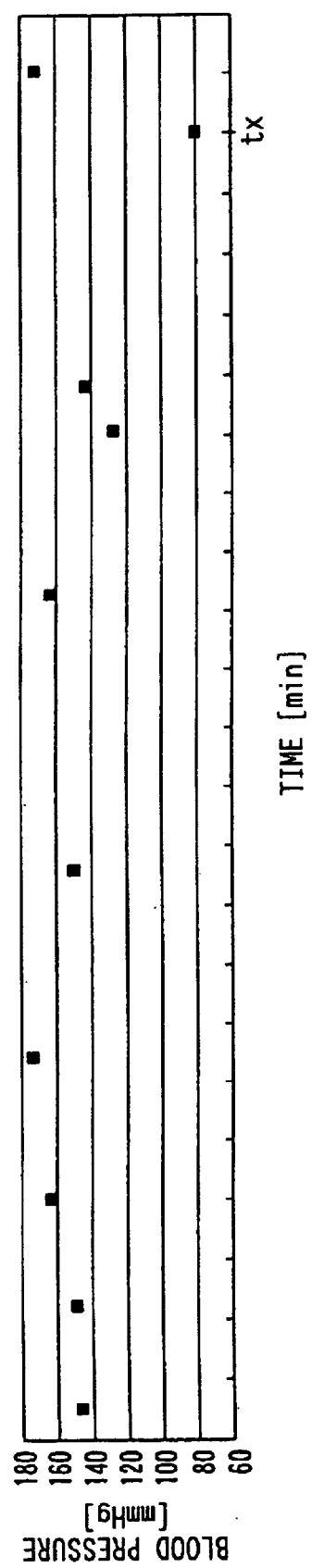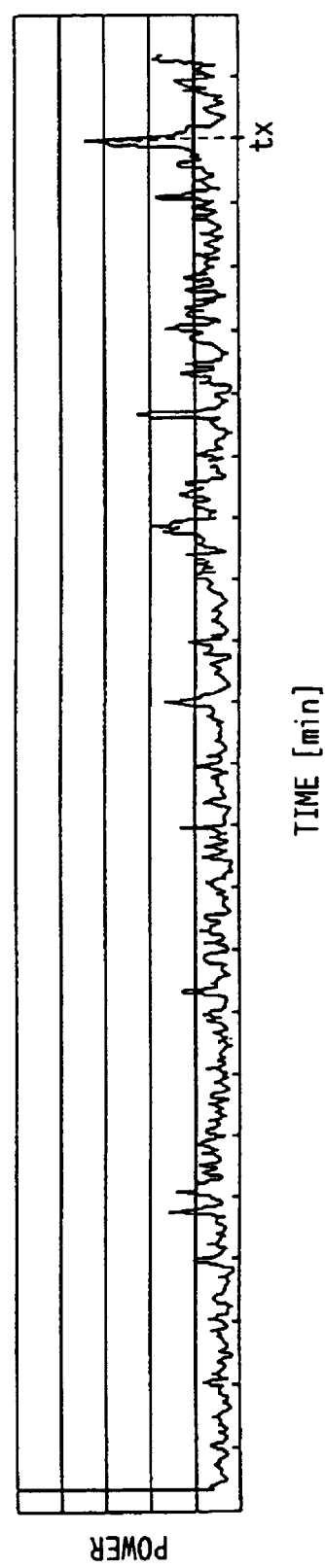

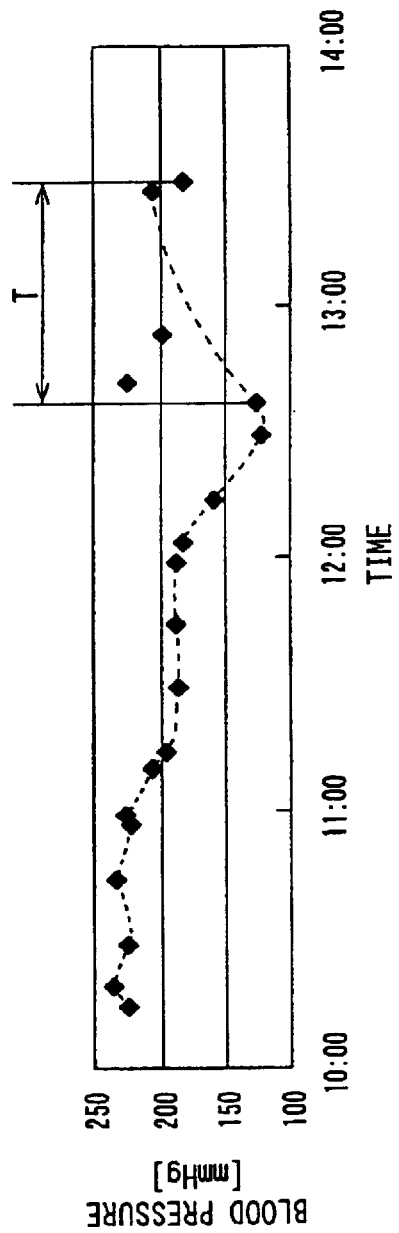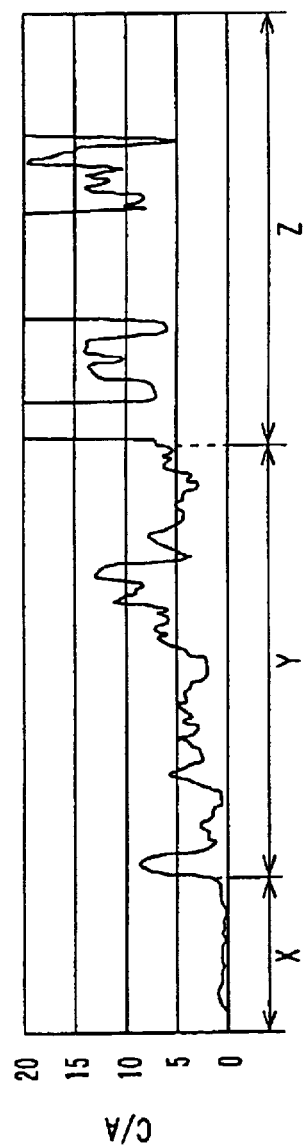

US 6,923,769 B2

METHOD AND APPARATUS FOR MONITORING BIOLOGICAL ABNORMALITY AND BLOOD PRESSURE

CROSS REFERENCE TO RELATED APPLICATION

This application is based on and incorporates herein by reference Japanese Patent Applications No. 2001-165297 filed May 31, 2001 and No. 2002-24056 filed Jan. 31, 2002.

FIELD OF THE INVENTION

The present invention is related to a clinical and physiological abnormality (biological abnormality) monitoring apparatus and method capable of predicting and sensing abnormal (unusual) clinical and physiological conditions based upon, for example, fluctuation of a blood flow rate or tissue blood volume. The present invention is also related to a blood pressure monitoring apparatus and method for predicting critical blood pressure changes.

BACKGROUND OF THE INVENTION

Conventionally, in order to prevent cardiovascular attacks such as syncope caused by rapid lowering of blood pressure in medical emergency fields and/or medical hemodialysis fields, blood pressure of patients is measured either in a continuous manner or in a certain constant interval. When the blood pressure is lowered, necessary medical treatments are carried out.

As methods of measuring blood pressure in these medical fields, there is such a method capable of noninvasively measuring blood pressure under noninvasive condition. As this noninvasive measuring method for blood pressure, the following measuring method has been proposed. That is, while a cuff is mounted on a major portion of body (for example, arm), Korotkoff sound caused by blood vessel is detected, which is caused by a pressure change occurring in the blood vessel, so as to estimate systolic and diastolic blood pressure values. Also, another method has been proposed in, for instance, U.S. Pat. No. 5,255,686 (JP-A-5-7558), in which cuff pressure is adjusted in response to a signal derived from a pressure sensor which detects cuff pressure. However, in these conventional methods, blood pressure cannot be monitored in a continuous manner.

It is proposed to avoid such a problem that in order to reduce loads given to a patient, when blood pressure of this patient is under stable condition, a blood pressure measuring operation is interrupted, whereas when the blood pressure is lowered (namely, only when blood pressure measurement is required), cuff pressure is applied to this patient so as to measure the changing blood pressure. However, there is no means capable of determining whether or not blood pressure of a patient is lowered without actually measuring the blood pressure. As a consequence, while cuff pressure is applied to the patient either in a continuous manner, or in an interrupt manner, the blood pressure thereof should be measured.

Also, in such a case that a patient is brought into a syncope state, since blood pressure of this patient is rapidly lowered, even when the blood pressure is monitored, an omen of this rapid-lowering blood pressure cannot be easily discovered. As a consequence, it is practically very difficult to discover such a blood pressure abnormality in an earlier stage.

SUMMARY OF THE INVENTION

The present invention has an object to provide a clinical and physiological abnormality monitoring apparatus capable of predicting and/or sensing a clinical and physiological abnormality without giving an excessive load to a person under measurement by performing a percutaneous measuring operation. Also, another object of the present invention is to provide a blood pressure monitoring apparatus capable of detecting a blood pressure abnormality by executing a percutaneous measuring operation, and capable of measuring blood pressure if necessary. A further object of the present invention is to provide a computer readable program, a recording medium, a clinical and physiological abnormality monitoring method, and a blood pressure monitoring method.

According to the first aspect of the present invention, a clinical and physiological abnormality monitoring apparatus and method detects vasomotion of a body in a percutaneous manner, and determines a clinical and physiological abnormality based on the detected vasomotion. According to the second aspect of the present invention, a blood pressure monitoring apparatus detects vasomotion of a body in a percutaneous manner, and measures a blood pressure based upon the detected vasomotion. In each apparatus and method, preferably, a change contained in a blood flow rates or the like in the blood vessel is detected to acquire a fluctuation of the blood rates caused by the vasomotion. The acquired fluctuation is used to determine the clinical and physiological abnormality and the blood pressure.

BRIEF DESCRIPTION OF THE DRAWINGS

For a better understanding of the present invention, a detailed description is made with in conjunction with the accompanying drawings. In the drawings:

FIG. 4A is a graph showing a blood pressure, and FIG. 4B is a graph showing a fluctuation amount of a low frequency component;

FIG. 9A is a graph showing temporal changes of blood pressure, and FIG. 9B is a graph showing changes of C/A;

Figure 1:
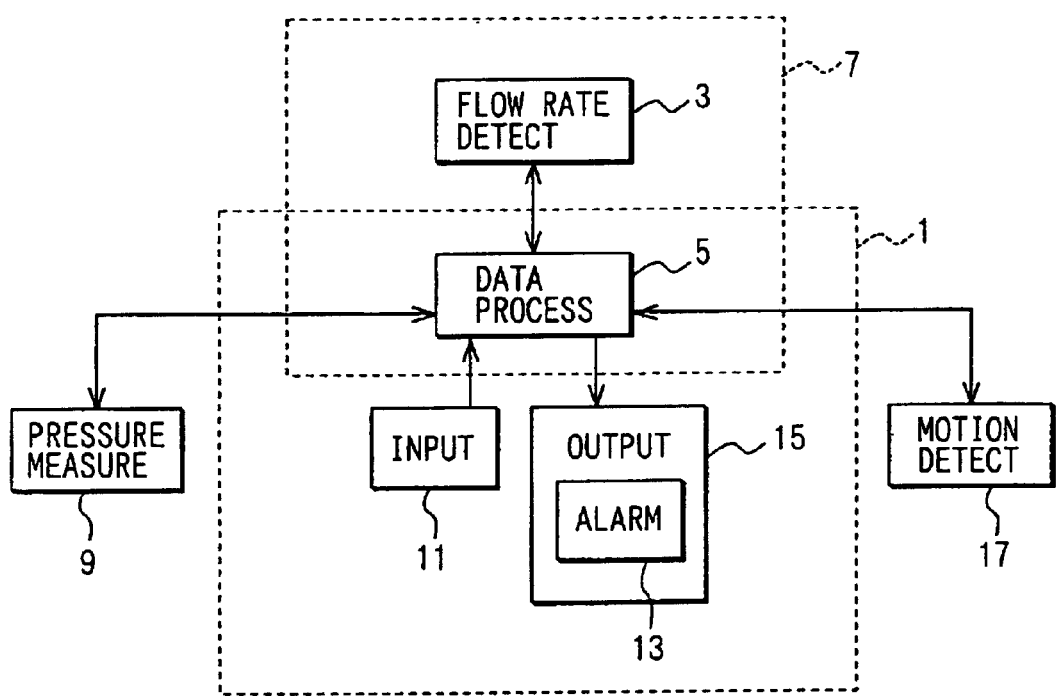
FIG. 1 is a block diagram of a blood pressure monitoring apparatus according to the first embodiment of the present invention.

DETAILED DESCRIPTION OF THE PREFERRED EMBODIMENTS (First Embodiment)

As a clinical and physiological abnormality monitoring apparatus capable of executing a clinical and physiological abnormal monitoring method, such a blood pressure monitoring apparatus (blood pressure abnormality monitor) is exemplified, by which a blood pressure abnormality of a body, or a living body (namely, a person to be measured such as a patient) can be predicted and/or sensed in accordance with a blood pressure monitoring method.

First, a basic structure of a blood pressure monitoring apparatus according to the first embodiment will now be explained with reference to FIG. 1.

This blood pressure monitoring apparatus is constituted by a main body 1 of this blood pressure monitoring apparatus stored in a housing, and various sorts of electric appliances connected to the blood pressure monitoring apparatus main body 1.

As a major construction, the blood pressure monitoring apparatus is provided with a skin blood flow rate detecting apparatus unit 7 containing both detecting unit 3 and data processing apparatus unit 5. The apparatus is further provided with a blood pressure measuring apparatus unit 9, an input unit 11, an output unit 15 including alarm issuing unit 13, and also, a body motion detecting apparatus unit 17.

In the skin blood flow amount detecting apparatus unit 7, a change in skin blood flow rates of a person to be measured, namely, blood flow rate change in blood vessels in the vicinity of skin, is percutaneous-detected, and a fluctuation of blood flow rates is acquired from this change in the blood flow rate caused by blood vessel motion, so that an abnormality of blood pressure is predicted and/or detected.

In response to an instruction issued from the skin blood flow rate detecting apparatus unit 1, the blood pressure measuring apparatus unit 9 measures blood pressure at an arm of a person under measurement and the like. It should be understood that as will be later explained with reference to the third embodiment, the blood pressure measuring apparatus unit 9 corresponds to such an apparatus in which, for example, a cuff is automatically actuated, and blood pressure is measured by using a pressure sensor mounted on this apparatus. This blood pressure measuring apparatus is well known in this field.

In the input unit 11, various sorts of setting values and the like are inputted in a manual manner. In the alarm issuing unit 13 of the output unit 15, an alarm is issued by way of sound and an indication in such a case that blood pressure measured by the blood pressure measuring apparatus 9 corresponds to a preset blood pressure abnormal value.

The body motion detecting apparatus unit 17 determines whether or not body motion of a person under measurement is detectable, and detects an occurrence of such body motion.

Next, the skin blood flow rate detecting apparatus unit 7 will now be explained more in detail.

The skin blood flow rate detecting apparatus unit 7 is equipped with the detecting unit 3 for detecting a skin blood flow rate while being mounted on a human body, and the data processing apparatus unit 5. This data processing apparatus unit 5 measures a change contained in blood flow rates based upon the skin blood flow rate detected by this detecting unit 3, and then, performs a frequency analysis and the like as to the detection result. It should also be noted that the data processing apparatus unit 5 is arranged by a microcomputer.

Figure 2A:
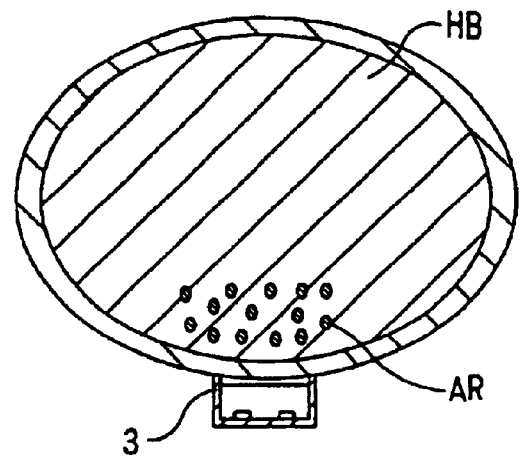
FIG. 2A is a schematic view of a human body.
Figure 2B:
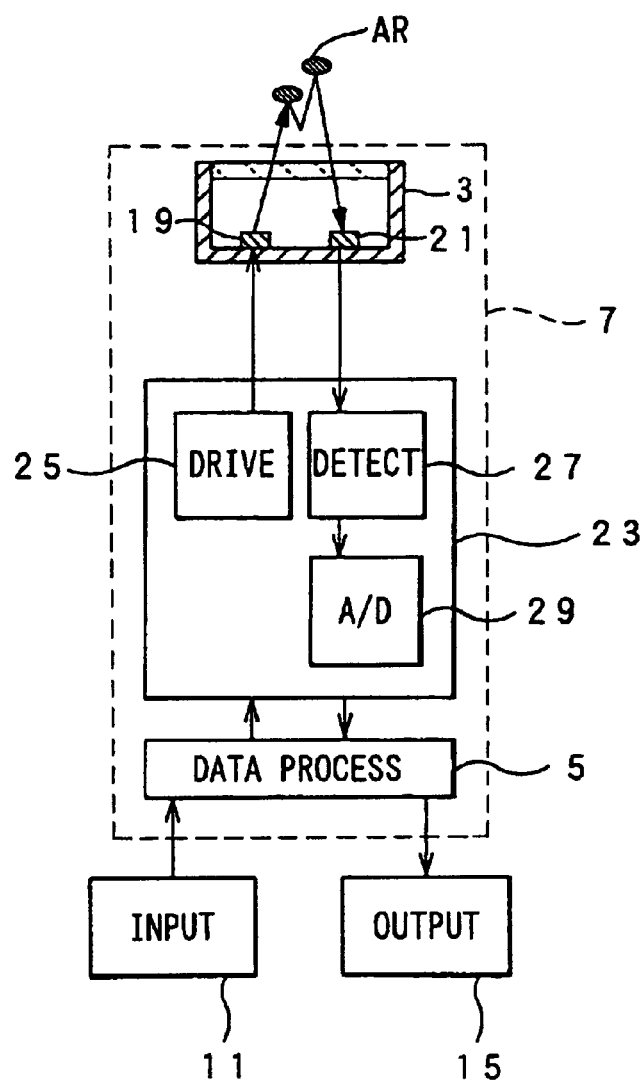
FIG. 2B is a circuit diagram showing the blood pressure monitoring apparatus according to the first embodiment.

As shown in FIGS. 2A and 2B, the detecting unit 3 corresponds to an optical type reflection-mode sensor well known in the technical field. This optical type reflection-mode sensor is equipped with a light emitting element (for instance, light emitting diode: LED) 19 and a light receiving element (photodiode: PD) 21. It should also be noted that since the detecting unit 3 detects the change contained in the blood flow rates as a change contained in pulse waves, this detecting unit 3 is referred to as a blood flow rate sensor or a pulse wave sensor.

Also, a circuit unit 23 connected to the detecting unit 3 is comprised of a drive circuit 25, a detecting circuit 27, and an A/D (analog-to-digital) converting unit 29. The detecting circuit 27 processes a detection signal derived from the detecting unit 3. The circuit unit 23 may input a drive condition and the like, and also may output detection data via the data processing apparatus unit 5 by operating either the input unit 11 or the output 15.

As this input unit 11, for example, a switch and the like such as a ten-keyboard (numerals enter keyboard) may be employed, whereas as the output unit 15, a display, a speaker, and the like may be used.

In the detecting unit 3, when light is irradiated from the light emitting element 19 toward a human body HB such as an arm, a portion of this irradiated light illuminates small arteries or arteriola (capillary arteries) AR which are penetrated through an interior of the human body HB, and then absorbed by hemoglobin contained in blood. The remaining light portion of this irradiated light is reflected and scattered by the small arteries, and then a portion of the reflected or scattered light is entered into the light receiving element 21. At this time, since an amount of hemoglobin existed in the small arteries is changed in a wave manner due to pulsation of the blood, the light which is absorbed by this hemoglobin is similarly changed in a wave manner. Also, an amount of hemoglobin is changed due to a change in diameters of blood vessels. As a result, an amount of received light is changed, which is reflected by the small arteries, so that the detecting unit 3 outputs this change contained in the light reception amounts as blood flow rate (blood flow amount) information (for example, voltage signal) to the detecting circuit 27.

The detecting circuit 27 amplifies the electric signal derived from the light receiving element 21, and then supplies the amplified electric signal to the A/D converting unit 29. The A/D converting unit 29 converts the analog signal into a digital signal, and then supplies this digital signal to the data processing apparatus unit 5.

The data processing apparatus unit 5 inputs thereinto the detection data from the detecting unit 3 so as to perform a blood flow rate analysis, and also controls both the drive circuit 25 and the detecting circuit 27. That is, this data processing apparatus unit 5 analyzes now the blood flow rate is changed. Also, the data processing apparatus unit 5 may instruct the blood pressure measuring apparatus unit 9 to start a blood pressure measuring operation, and also to output an instruction of cuff measuring pressure, and also may input a blood pressure value, a blood pressure measuring time instant, and the like. Furthermore, while a signal derived from the body motion detecting apparatus unit 17 is entered thereinto, the data processing apparatus unit 5 may determine whether body motion occurs. Then, in the case that the data processing apparatus unit 5 determines an occurrence of a blood pressure abnormality based upon these values, this data processing apparatus unit 5 may supply an instruction of an alarm command to the alarm issuing unit 13. That is, the data processing apparatus unit 5 may execute calculation process operations of the blood pressure monitoring apparatus of this embodiment, for instance, may grasp the change contained in the blood flow rates, and may execute the determination of starting/instructing the blood pressure measuring operations.

It should be noted that the data processing apparatus unit 5 may be provided in conjunction with, for example, the blood pressure measuring apparatus unit 9 other than the skin blood pressure rate detecting apparatus unit 1. Alternatively, the alarm issuing unit 13 may be provided in conjunction with the blood pressure measuring apparatus unit 9 as a separate unit with respect to the output unit 15.

Also, in this embodiment, as the detecting unit 3, such a detecting unit 3 capable of acquiring the change contained in the blood flow rates from the change contained in the hemoglobin amounts which are involved in the small arteries of the skin is employed. The method capable of grasping a change in skin blood flow rates is not limited to the above method. For instance, a pulse oxymeter and a blood flow rate sensor which utilize an absorption characteristic of hemoglobin may be alternatively employed. Also, an ultrasonic blood flow meter and a laser Doppler blood flow meter, which are capable of acquiring a change contained in blood flow rates based upon a blood flow velocity may be used.

Next, a description will now be made of a blood flow rate analyzing algorithm executed in the data processing apparatus unit 5.

In this analyzing algorithm, a fluctuation amount of blood flow rates (bloodstream amounts) of a frequency component which is lower than a frequency component equivalent to a pulse interval is calculated from a blood flow rate signal of arbitrary time.

Figure 3A:
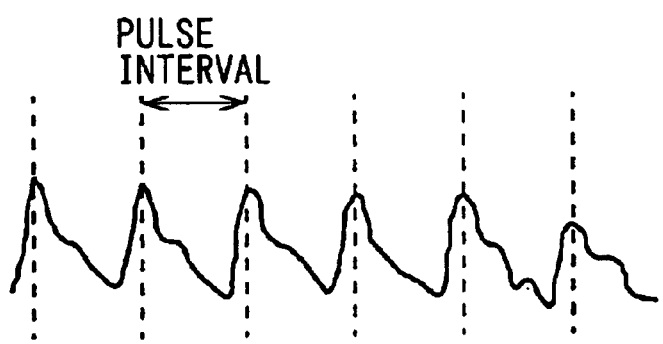
FIG. 3A is a graph showing a pulse wave signal.

In this case, first, when pulses for arbitrary time are measured by employing the detecting unit 3, for example, as indicated in FIG. 3A, a pulse wave signal (blood flow rate signal) is obtained, the pulse wave of which is continued. Within this pulse wave signal, pulse waves indicated by individual pulsations correspond to respective pulses. It should also be noted that an interval between a peak of a pulse wave and another peak of another pulse wave will be called as a "pulse interval."

Figure 3B:
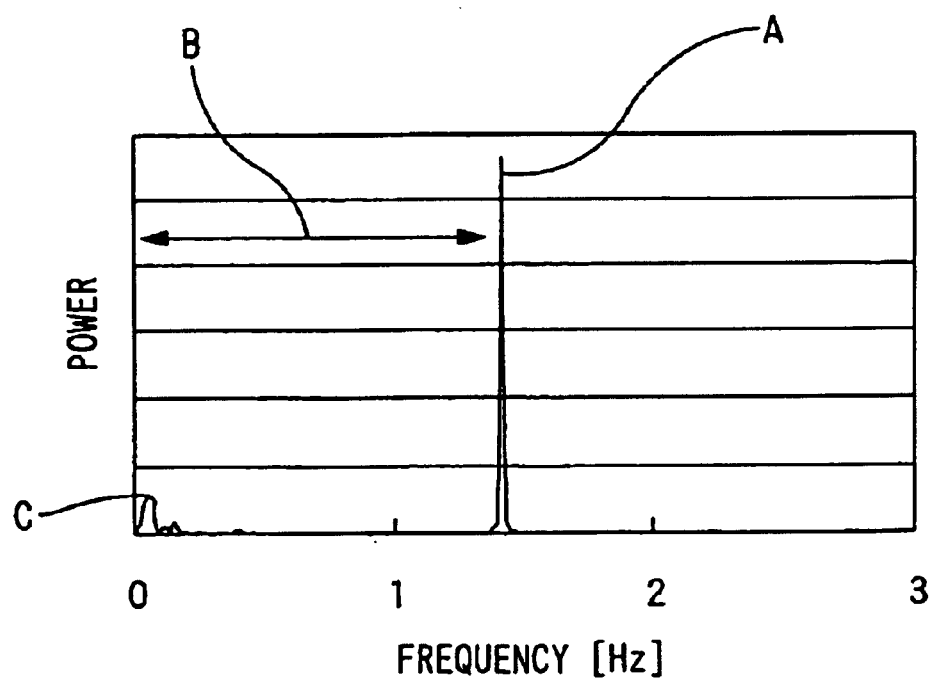
FIG. 3B is a graph showing a result of frequency-analyzing the pulse. wave signal.

Then, the data processing apparatus unit 5 executes the frequency analysis (for example, FFT (fast Fourier Transform) analysis well known in this field) with respect to the acquired pulse wave signal, and thus acquires a power spectrum of the low frequency component C corresponding to the fluctuation of the blood flow rates, as indicated in FIG. 3B.

An amplitude value of this power spectrum corresponds to the fluctuation amount of the low frequency components. Thus, the low frequency component fluctuation amount can be continuously grasped from a temporal change of this amplitude value. It should be understood that, as represented in FIG. 3B, a power spectrum of a frequency component A corresponding to a pulse interval appears on the side of a high frequency, as compared with the power spectrum of the low frequency component C.

A fluctuation amount of low frequency components may grasp not only a change in blood flow rates caused by pulsations every one cardiac beat of a heart, but also may grasp a change in diameters of a blood vessel under observation, and further a change in blood flow rates, which is caused by adverse influences given by blood vessels located up to a place under observation. However, it is so conceived that this fluctuation amount of the low frequency components may mainly indicate such a change contained in blood flow rates, which is caused by vasomotion.

In the case that this value is continuously monitored, for example, as shown in FIGS. 4A and 4B, when lowering of blood pressure occurs, a large change at time tx may be observed, which is known from experimental observations.

As a result, when this change in the low frequency components is observed, a certain blood pressure abnormality may be predicted. As a consequence, while the data processing apparatus unit 5 instructs the blood pressure measuring apparatus unit 9 to commence the measuring operation of the blood pressure, so that a blood pressure value of a patient can be grasped by the blood pressure abnormality monitoring apparatus.

Next, an overall process operation of blood pressure monitoring operation by the blood pressure monitoring apparatus of this embodiment will now be described with reference to a flow diagram of FIG. 5.

Figure 5:
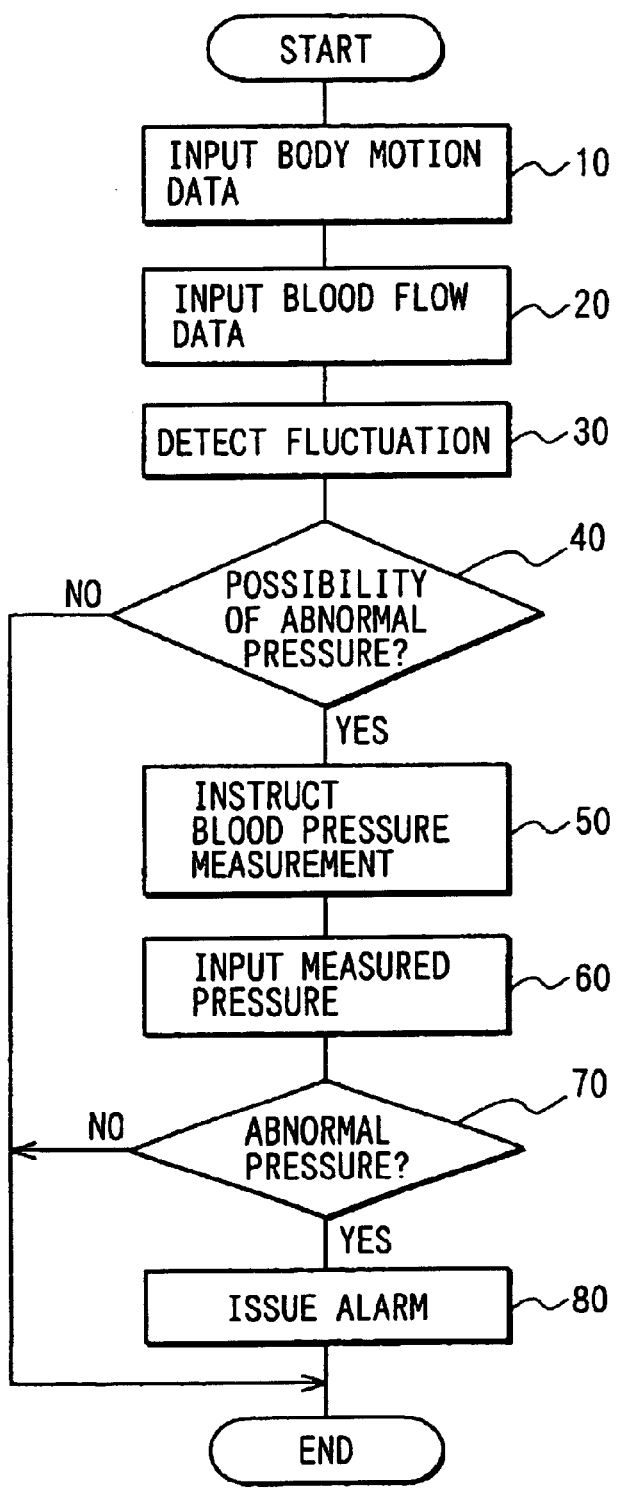
FIG. 5 is a flow diagram of a process operation capable of detecting a blood pressure abnormality in the first embodiment.

As indicated in FIG. 5, at step 10, data related to body motion detected by the body motion detecting apparatus unit 17 is inputted into the data processing apparatus unit 5. At the subsequent step 20, data as to a blood flow rate detected from the detecting unit 3 is entered into the data processing apparatus unit 5. At the next step 30, the data processing apparatus unit 5 detects a fluctuation contained in skin blood flow rates. Specifically, this data processing apparatus unit 5 executes a frequency analysis with respect to a pulse wave signal derived from the detecting unit 3 so as to detect a fluctuation contained in blood flow rates (that is, fluctuation amount of low frequency components).

At the subsequent step 40, this data processing apparatus unit 5 determines whether a blood pressure abnormality may be expected based upon the above data as to the fluctuation of the blood flow rates. That is, the data processing apparatus unit 5 determines whether the fluctuation of the blood flow rates is higher than, or equal to a predetermined threshold reference value.

Then, in such a case that the blood pressure abnormality is expected, the skin blood flow rate detecting apparatus unit 7 instructs the blood pressure measuring apparatus unit 9 to measure blood pressure at step 50. At step 60, in response to this instruction, the blood pressure measuring apparatus unit 9 measures the blood pressure, and then this measurement value is inputted into the data processing apparatus unit 5.

At step 70, the data processing apparatus 5 determines whether the measurement value of the blood pressure acquired from the blood pressure measuring apparatus unit 9 corresponds to a preset blood pressure abnormal value.

In this case, when the data processing apparatus unit 5 determines that the blood pressure abnormality occurs, at step 80, the data processing apparatus unit 5 instructs the alarm issuing unit 13 to issue an alarm command, so that the alarm issuing unit 13 issues an alarm.

As previously described in detail, while the detecting unit 3 corresponding to the optical type reflection mode sensor is employed so as to measure the blood flow rate in the percutaneous manner, the fluctuation amount of the blood flow rates of the frequency component lower than such a frequency component equivalent to the pulse interval is calculated. In the case that this fluctuation amount is larger than, or equal to a predetermined threshold value, the blood pressure is measured. In the case that the actually measured blood pressure becomes the abnormal blood pressure, this blood pressure abnormality is notified. As a consequence, this blood pressure monitoring apparatus can notify such a blood pressure abnormality to either the patient himself or the nursing staff, so that necessary treatments can be taken.

Accordingly, in accordance with this embodiment, since the blood pressure monitoring apparatus can predict and/or sense the blood pressure abnormality without giving excessive loads to the patient. Furthermore, it can actually measure the blood pressure, such a particular effect can be achieved that the blood pressure monitoring apparatus can correctly determine the blood pressure abnormality.

(Second Embodiment)

The basic arrangement of the blood pressure monitoring apparatus according to the second embodiment is similar to that of the first embodiment. A pulse wave sensor is employed as the detecting unit 3.

In this embodiment, a blood pressure abnormality is sensed and notified by utilizing a fluctuation of a base line of. a pulse wave signal (envelope line of pulse wave signal).

When time sequential data of a pulse wave equal to the above pulse wave signal is frequency-analyzed, a frequency component contained in this pulse wave signal is obtained.

In the case that the above frequency characteristic shown in FIG. 3B is obtained by executing the frequency analysis, the A-frequency components (for example, 0.3 Hz to 3 Hz) corresponding to the respective pulses appear in A of FIG. 3B. It should be noted that as to a peak of the A-frequency components in this case, a center frequency thereof is approximately 1.5 Hz, and pulse interval is approximately 670 msec.

On the other hand, the C-frequency components (for example, lower than, equal to 0.25 Hz) lower than the A-frequency components corresponding to the respective pulses appear within such a frequency range of the region B shown in FIG. 3B. This C-frequency component indicates a fluctuation contained in pulse wave signals, which corresponds to a blood pressure abnormality, for instance, a large increase in blood pressure, and a large decrease in blood pressure.

On the other hand, in the case that a body is under normal condition, the above frequency characteristic is varied, depending upon an individual and an occasional case. However, for example, since a peak value C of the C-frequency components cannot be observed, there is such a phenomenon that a ratio C/A of the peak value C contained in the C-frequency components to the peak value C contained in the A-frequency components is not largely changed.

Figure 6A:
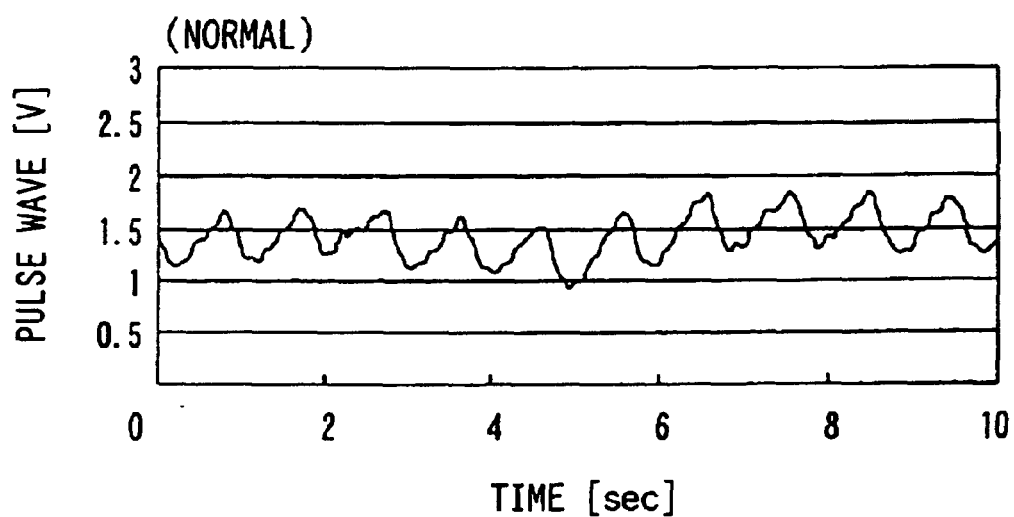
FIG. 6A is a graph showing a pulse wave signal during rest time.
Figure 6B:
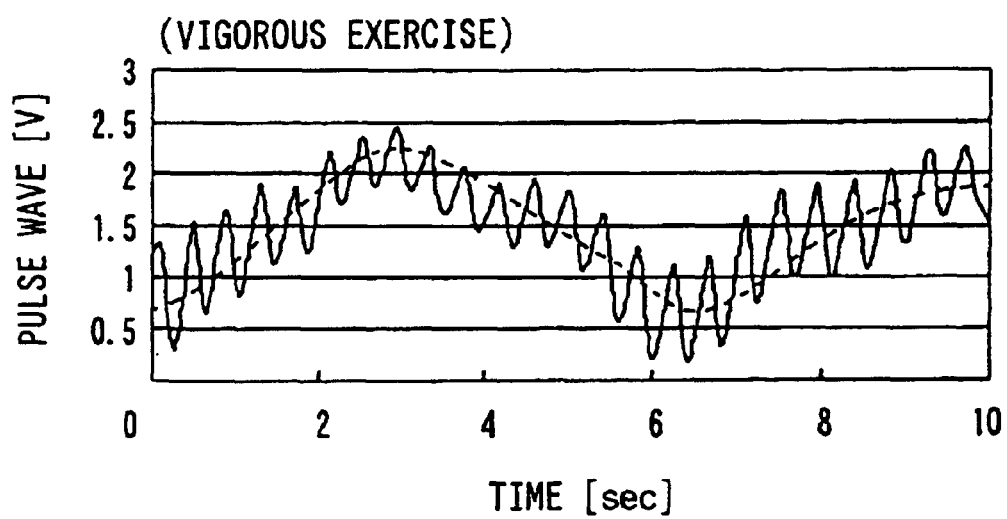
FIG. 6B is a graph showing a pulse wave signal during vigorous exercise.

However, when the blood pressure abnormality occurs, for example, when the blood pressure is largely increased and/or decreased, the balance of these peak values (that is, above C/A) becomes different. For instance, as represented in FIG. 6A, a pulse wave signal under normal condition (averaged blood pressure: 125 mmHg) is not substantially completely fluctuated along upper/lower directions, as apparent from a base line (formed by average of maximum and minimum peaks) or envelope line (formed by maximum or minimum peak) of this pulse wave signal. When a body vigorously exercises, as shown in FIG. 6B, a heart rate is increased, a pulse interval becomes short, and blood pressure is increased (averaged blood pressure: 175 mmHg). Furthermore, a fluctuation occurs in the base line (dotted line in FIG. 6B) of the pulse wave signal.

It is so conceived that this fluctuation contained in the base lines is caused by movement of blood vessels. This fact may be conceived by the following aspect. That is, in order to improve an abnormality of blood flow rate balance within the interior of the body, the body compresses capillary arteries to adjust the blood flow rate. As a consequence, it is so conceived that this may grasp a change in hemoglobin amounts with the capillary arteries, which is caused by a change in vessel diameters of the capillary arteries.

Figure 7A:
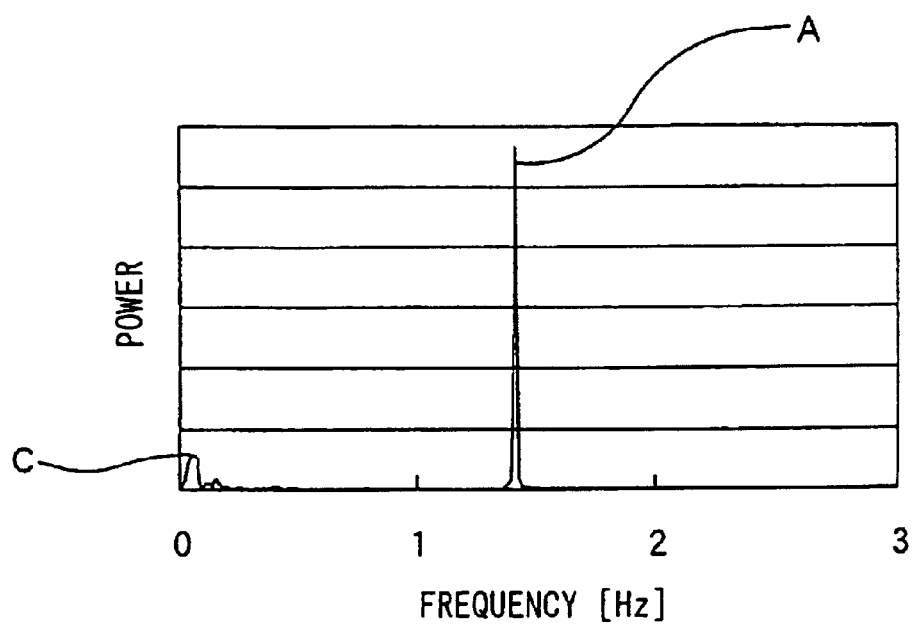
FIG. 7A is a graph showing a frequency component during rest time.
Figure 7B:
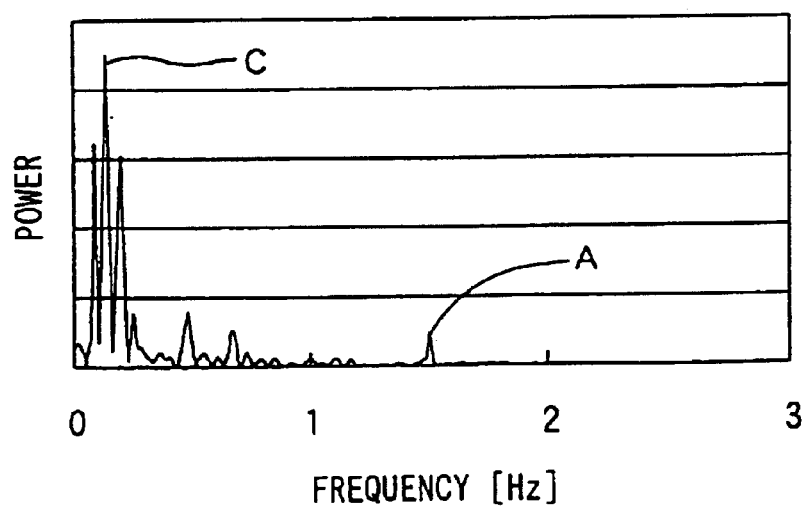
FIG. 7B is a graph showing a frequency component during vigorous exercise.
Figure 8A:
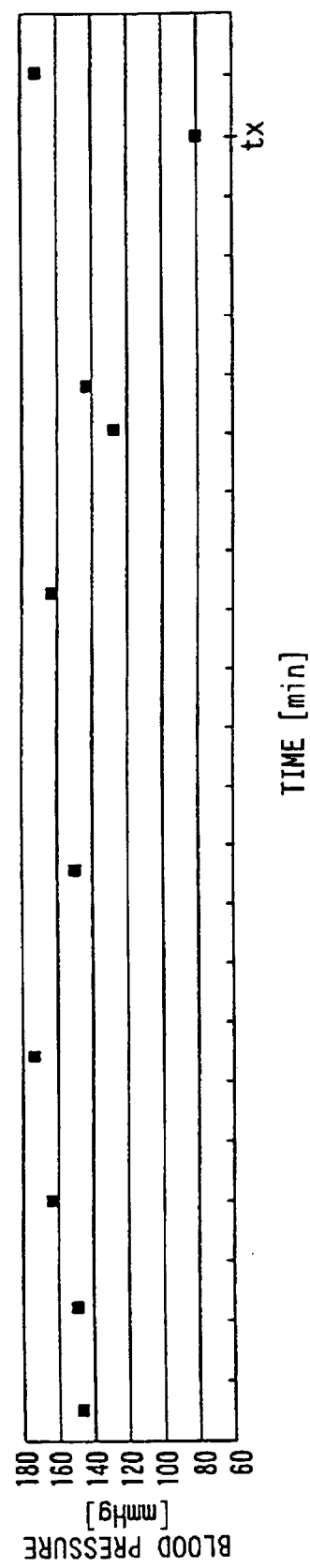
FIG. 8A is a graph showing temporal changes of blood pressure.
Figure 8B:
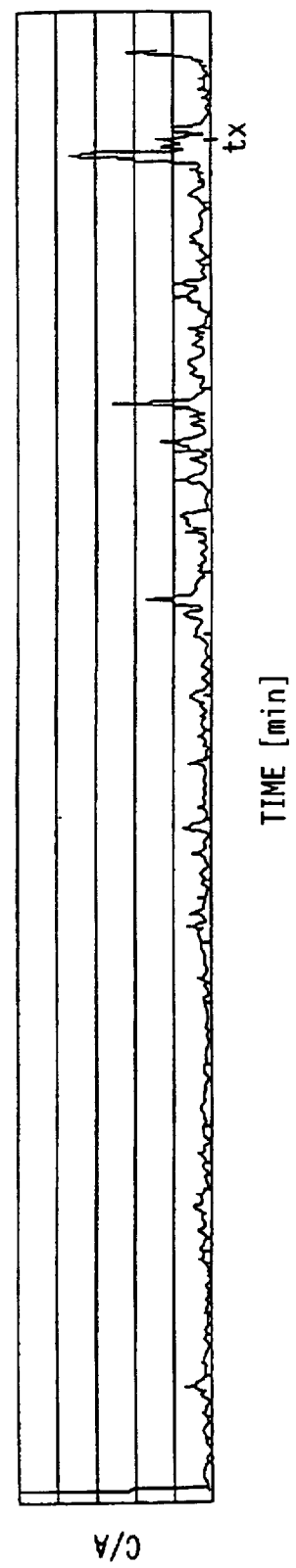
FIG. 8B is a graph showing changes of C/A.

Then, the data indicated in FIGS. 6A and 6B is frequency-analyzed, and this frequency-analyzed result is shown in FIGS. 7A and 7B. FIGS. 7A and 7B indicate such a result that both the pulse wave signal obtained before the blood pressure is increased, and the pulse wave signal obtained after the blood pressure is decreased are frequency-analyzed. A ratio C/A obtained in the case that a blood pressure abnormality (that is, blood pressure is increased) is present (FIG. 7B) is largely changed with respect to a ratio C/A obtained in the case that blood pressure is under normal condition (FIG. 7A). That is, when the blood pressure abnormality caused by the increased blood pressure is present, it can be seen that the ratio C/A is gradually increased.

Also, FIGS. 8A, 8B and FIGS. 9A, 9B indicate both a change contained in blood pressure in the case that a blood pressure abnormality caused by lowering blood pressure is present, and also a transition of the ratio C/A of the above peak values C and A corresponding to this blood pressure change. As apparent from these figures, the ratio C/A is increased in connection with the abnormal decrease of the blood pressure.

It should be noted that numeral values of the ratio C/A indicated in an ordinate of FIG. 9B show that the peak value C becomes certain times larger than the peak value A. In FIG. 9B, when the ratio C/A is smaller than 5 times, this range X indicates that the blood pressure is normal. When the ratio C/A exceeds 5 times, this range Y indicates that the blood pressure abnormality can be predicted. A range Z subsequent to this range Y indicates that lowering of blood pressure actually and apparently occurs. Therefore, the blood pressure cannot be measured accurately in the time range T shown in FIG. 9A.

As a consequence, the blood pressure abnormality can be predicted and sensed by checking this ratio C/A.

Figure 10:
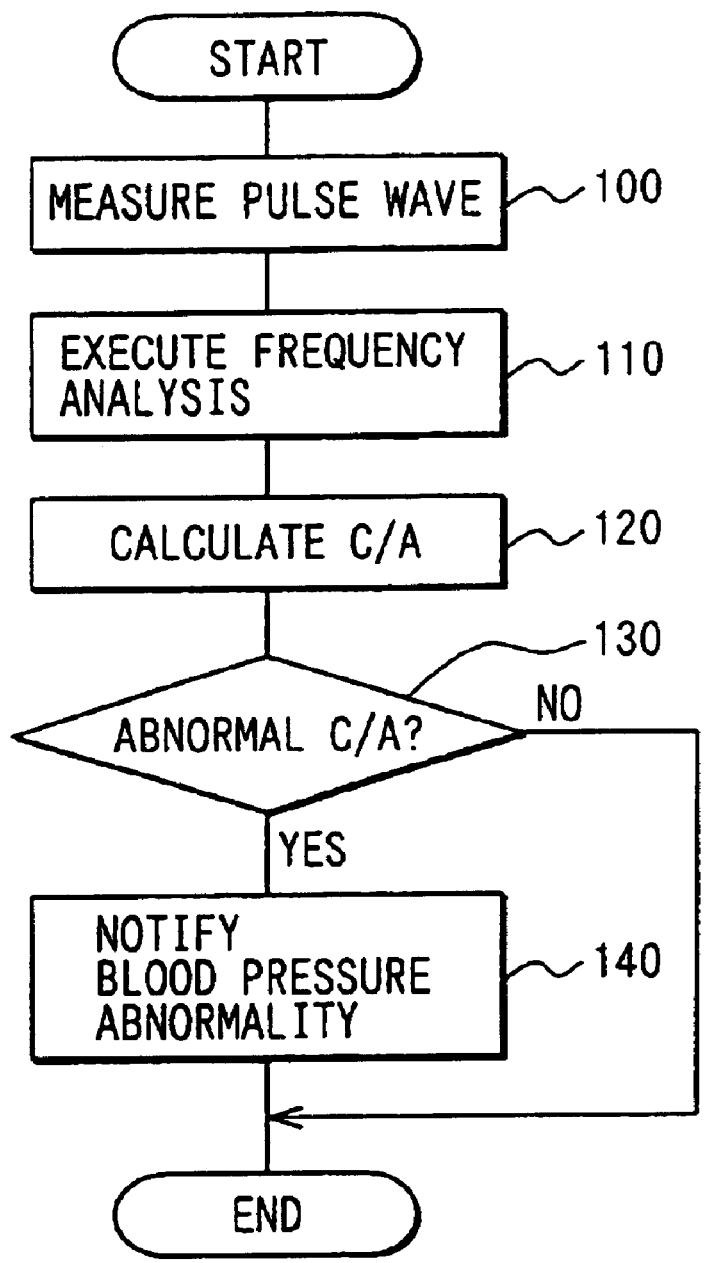
FIG. 10 is a flow diagram of a process operation capable of detecting a blood pressure abnormality in the second embodiment of the present invention.

Referring now to a flow diagram shown in FIG. 10, a control process operation of the second embodiment is described, which is carried out in accordance with the above basic idea and sequential operation.

As indicated in the flow diagram of FIG. 10, for example, when an exercise is first commenced, a measurement of pulse waves is commenced at step 100. Specifically, a signal derived from the pulse wave sensor 3 is A/D-converted to digital data, and then, this digital data is entered into the data processing apparatus unit 5.

Subsequently, at step 110, the data processing apparatus unit 5 executes a frequency analysis such as FFT with respect to the digitally-converted signal (that is, pulse wave signal) supplied from the pulse wave sensor 3, that is, time sequential data of pulse waves so as to acquire both A-frequency components corresponding to the respective pulse waves, and fluctuation components (C-frequency components) of such pulse wave signals corresponding to pulse wave streams, the frequency of which is lower than that of the A-frequency components.

It should be understood that this C-frequency component corresponds to a fluctuation component of a base line (otherwise, envelope line) of the pulse wave signal. Specifically, this C-frequency component corresponds to such a low-frequency component within a predetermined range which is obtained by frequency-analyzing the pulse wave signal, for example, within a frequency range lower than, or equal to 0.5 Hz (preferably, lower than, equal to 0.25 Hz), that is, 0 Hz to 0.25 Hz.

At the subsequent step 120, a ratio C/A is calculated, that is, a ratio as to power (peak value A) of such a peak (maximum peak) of the A-frequency components indicative of the respective pulse waves with respect to power (peak value C) of such a peak (maximum peak) of the C-frequency components.

At the next step 130, the data processing apparatus unit 5 determines whether a blood pressure abnormality is present by checking whether the above ratio C/A as to these peak values C and A is larger than, or equal to a predetermined threshold value.

For instance, the data processing apparatus unit 5 determines whether such a blood pressure abnormality is present by checking how many times the ratio C/A of the peak value A to the peak value C, which are presently measured, becomes larger than the ratio C/A acquired during rest period. If the determination result becomes YES in this step 130, then the control process operation advances to step 140. On the contrary, if the determination result becomes NO, then this control process operation is once accomplished.

It should also be noted that as previously described, the above ratio C/A is also changed before the actual blood pressure abnormality occurs. As a result, since the threshold value is properly set, the occurrence of the blood pressure abnormality may be predicted. For instance, since the ratio C/A is set to be smaller than the threshold value used to predict the blood pressure abnormality by a preselected value, such a blood pressure abnormality may be predicted.

At step 140, since it can be regarded that the blood pressure abnormality is present (also, since blood pressure abnormality can be predicted in case of prediction), this fact is displayed so that this blood pressure abnormality is notified to a person of interest, or neighbors. Then this control process operation is once ended.

As explained in detail, in accordance with this second embodiment, while the pulse waves of the person under measurement are measured by the pulse wave sensor 3, the frequency analysis is carried out with respect to this continuous pulse wave signal so as to calculate the ratio C/A. Normally, the ratio C/A of the peak value C of the C-frequency components which indicate the fluctuation of the base line (or envelope line) of the above pulse wave signal with respect to the peak value A of the A-frequency components which represent the respective pulse waves is acquired. Then, a determination is made whether the blood pressure abnormality is present, or can be predicted based upon this ratio C/A.

As a consequence, since it is possible to correctly sense that the blood pressure abnormality is present, when the blood pressure abnormality actually occurs, this fact is notified. Thus, a certain treatment is carried out, for example, the exercise is stopped, so that safety aspects related to the person under measurement can be improved.

Also, for example, even under such a condition that the blood pressure is rapidly lowered, in accordance with this embodiment, this condition can be surely detected, and the blood pressure abnormality can be predicted. Therefore, the superior monitoring method with the high safety performance can be realized without passing up an omen of lowering of the blood pressure.

Moreover, in this embodiment, since the blood pressure abnormality may be sensed (or predicted) based upon the ratio C/A, the cuff pressure is no longer applied for a long time in the continuous manner, as compared with the conventional manner using only the cuff. As a consequence, the monitoring method of this embodiment is very preferable for the person under measurement with applying a little of pain.

Also, in general, while the close contact condition between the human body and the pulse wave sensor 3 is not always constant, but is temporally changed, the fluctuation amount of the frequency components is changed due to the above adverse influences. Therefore, the correct prediction of the blood pressure abnormality can be hardly carried out. However, in accordance with the blood pressure monitoring apparatus of this embodiment, since the blood pressure abnormality can be sensed (or can be predicted) based upon the ratio C/A, such an adverse influence caused by the condition under which the pulse wave sensor 3 is mounted on the skin can be reduced.

(Third Embodiment)

The blood pressure monitoring apparatus according to the third embodiment executes a blood pressure measurement using a cuff in the case that a blood pressure abnormality may be predicted and/or sensed with employment of a pulse wave sensor.

Figure 11A:
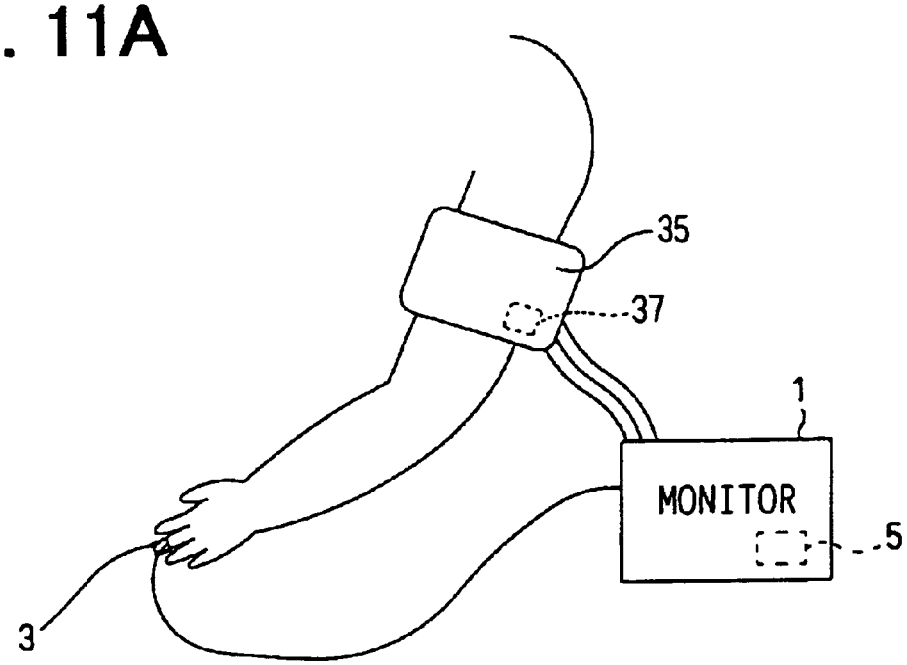
FIGS. 11A and 11B are schematic views showing a conceptual structure of a blood pressure monitoring apparatus according to the third embodiment of the present invention.

As indicated in FIG. 11A, the blood pressure monitoring apparatus is provided with the main body 1 of the blood pressure monitoring apparatus, while the main body 1 is equipped with the data processing apparatus unit 5 and the like, which is constructed of a microcomputer. In this blood pressure monitoring apparatus, the pulse wave sensor 3 is mounted on a finger tip of a person under measurement so as to detect pulse waves. While a cuff 35 capable of automatically adjusting cuff pressure is mounted on an arm of this person under measurement, blood pressure is detected by operating a pressure sensor 37 arranged in this cuff 35.

Figure 11B:
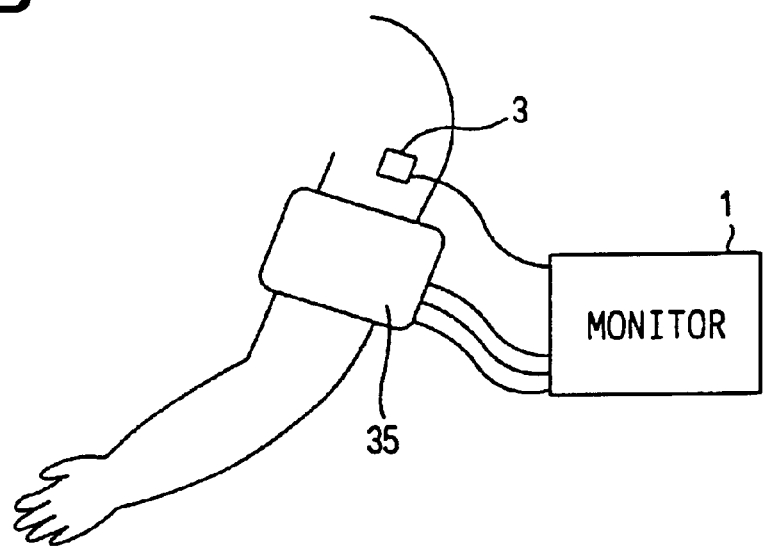

Alternatively, as shown in FIG. 11B, the position where the pulse wave sensor 3 is mounted is not limited to the finger chip, but the pulse wave sensor 3 may be mounted on an arm and the like.

It should be noted that as to such a method that this cuff 35 capable of adjusting the cuff pressure is mounted so as to detect the blood pressure, for instance, the above technology disclosed in U.S. Pat. No. 5,255,686 (JP-A-5-7558) may be employed.

In this embodiment, a pulse wave signal acquired by the pulse wave sensor 3 is processed by the data processing apparatus unit 5, so that a blood pressure abnormality may be predicted and/or sensed based upon the above ratio C/A. Then, in the case that the blood pressure abnormality is predicted and/or sensed, such a control operation for increasing the cuff pressure is carried out, and also, blood pressure at a portion of the arm on which the cuff 35 is mounted is measured.

Figure 12:
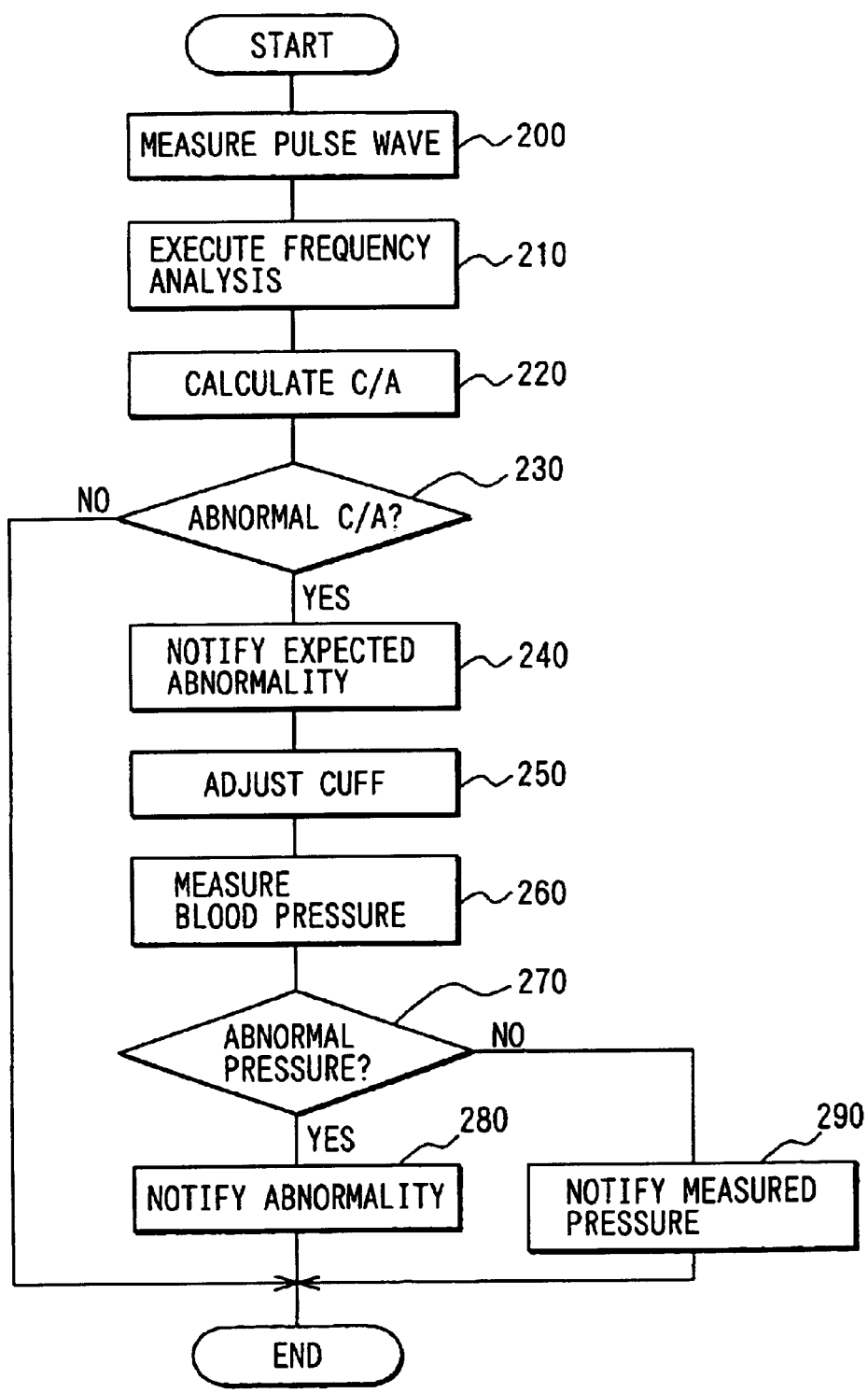
FIG. 12 is a flow diagram showing a process operation capable of detecting a blood pressure abnormality in the third embodiment.

Next, a process operation executed in the data processing apparatus unit 5 of this embodiment will now be explained based upon a flow diagram of FIG. 12.

As indicated in this flow diagram, a measurement of pulse waves is firstly commenced by employing the pulse wave sensor 3 at step 200.

Subsequently, at step 210, the data processing apparatus unit 5 executes a frequency analysis with respect to the pulse wave signal supplied from the pulse wave sensor 3 so as to acquire both A-frequency components corresponding to the respective pulse waves, and fluctuation components (C-frequency components) of such pulse wave signals corresponding to pulse wave streams, the frequency of which is lower than that of the A-frequency components. At the subsequent step 220, a ratio C/A is calculated, that is, a ratio as to power (peak value A) of such a peak of the A-frequency components indicative of the respective pulse waves with respect to power (peak value C) of such a peak of the C-frequency components.

At the next step 230, the data processing apparatus unit 5 determines whether a blood pressure abnormality is present by checking whether the above ratio C/A is abnormal (larger than or equal to a predetermined threshold value). If the determination result becomes YES in this step 230, then the process operation advances to step 240. To the contrary, if the determination result becomes NO, then this control operation is once accomplished.

It should also be noted that this determination as to the blood pressure abnormality may involve not only such a determination as to the blood pressure abnormality, but also another determination as to the prediction of the blood pressure abnormality.

At the step 240, since it can be regarded that the blood pressure abnormality is present, a process operation for notifying this fact is carried out. For example, such a message that blood pressure abnormality might be expected is indicated on, for instance, a display of the output unit 15. Alternatively, such a fact may be notified by producing electronic sound.

At the subsequent step 250, a process operation for adjusting cuff pressure is carried out. At the next step 260, blood pressure is measured based upon a sensor signal derived from the pressure sensor 37.

At the next step 270, the data processing apparatus unit 5 finally determines whether a blood pressure abnormality is present based upon the blood pressure measurement result obtained by the pressure sensor 37. If the determination result becomes YES, then the process operation advances to a further step 280. To the contrary, if the determination result becomes NO, then the process operation advances to step 290.

Since the data processing apparatus unit 5 finally determines that the blood pressure abnormality is present in the step 280, this fact is indicated, or notified by producing an alarm. Then, this process operation is once ended.

On the other hand, since the data processing apparatus unit 5 finally determines that the blood pressure abnormality does not occur in the step 290, another process operation is carried out by which such a content that blood pressure is increased is displayed. Then, this process operation is once accomplished.

In accordance with this embodiment, not only the blood pressure abnormality may be predicted/sensed from the data of the pulse wave signal obtained by employing the pulse wave sensor 3, but also the blood pressure may be measured by employing both the cuff 35 and the pressure sensor 37 in the case that such a blood pressure abnormality is predicted/sensed.

As a consequence, in accordance with this embodiment 3, the following effect can be achieved in addition to the effect achieved by the first embodiment. That is, the blood pressure abnormality can be predicted/sensed in higher precision.

It should be understood in this embodiment that when the blood pressure abnormality is predicted/sensed by using the pulse wave signal, the cuff pressure is automatically adjusted to detect the blood pressure. Alternatively, in such a case that the blood pressure abnormality is predicted/sensed based upon the pulse wave signal, upon receipt of this notification, blood pressure may be detected in a manual manner.

(Fourth Embodiment)

In this fourth embodiment, while a change contained in fluctuation amounts of blood flow rates as to lower frequency components than such a frequency component equivalent to a pulse interval is acquired, a value of the above fluctuation amounts is compared with a value of fluctuation amounts of low frequency components obtained when a measurement is commenced. Thus, the blood pressure monitoring apparatus may grasp a degree of increase of the fluctuation amounts.

Figure 13:
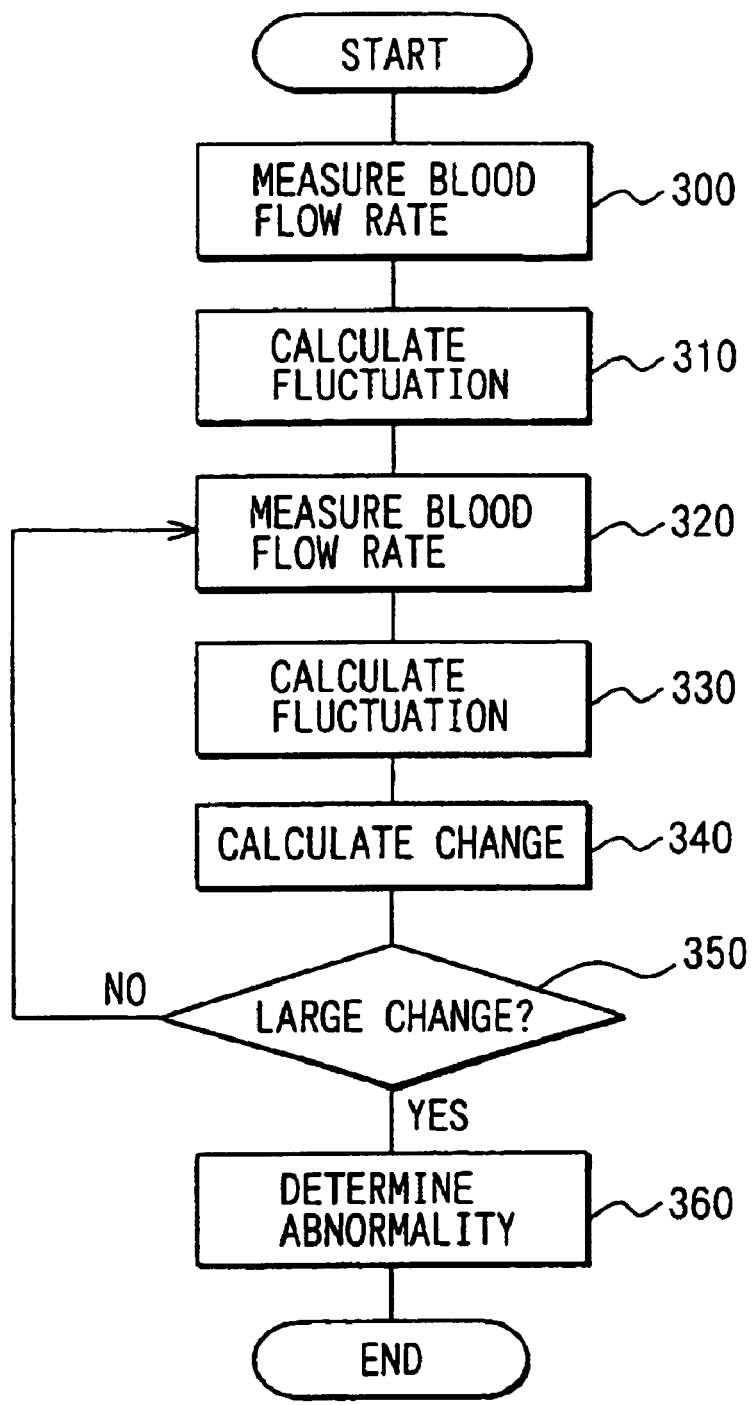
FIG. 13 is a flow diagram showing a process operation capable of detecting a blood pressure abnormality according to the fourth embodiment of the present invention.

FIG. 13 is a flow diagram for explaining process operations of the blood pressure monitoring apparatus. At first, at step 300, a blood flow rate is measured based upon a pulse wave signal.

At the next step 310, a fluctuation amount of low frequency components when the measuring operation is commenced is calculated. For instance, such an averaged value of fluctuation amounts acquired during several seconds to several minutes while the measuring operation is carried out under sufficiently stable condition is employed.

At the subsequent step 320, blood flow rates after the measuring operation is commenced (that is, during measurement) are continuously measured. At the next step 330, fluctuation amounts of low frequency components during the measuring operation are continuously calculated. At the subsequent step 340, a calculation is made of a difference between the fluctuation amount obtained when the measuring operation is commenced and the fluctuation amount acquired during the measuring operation. That is, a calculation of a change amount contained in the fluctuation amounts which have. been acquired after the measuring operation was commenced.

At the next step 350, the change amount (calculation value) of these fluctuation amounts is compared with a predetermined threshold value.

In the case that the change amount of the fluctuation amounts is smaller than the threshold value, the data processing apparatus unit 5 determines that there is no clinical and physiological abnormality (no blood pressure abnormality). The process operation returns to the previous step 320. On the other hand, in the case that the change amount of the fluctuation amounts is larger than or equal to the threshold value, the data processing apparatus unit 5 determines that a clinical and physiological abnormality (blood pressure abnormality) is present and indicates it at step 360.

This determination is properly carried out, which may be confirmed from the following fact. That is, as indicated in FIGS. 4A and 4B, in such a case that the blood pressure is lowered, as compared with the blood pressure when the measuring operation is commenced, the fluctuation amount of the low frequency components is largely increased, as compared with the fluctuation amount obtained when the measuring operation is started.

In accordance with this embodiment, since the blood pressure abnormality is detected based upon the change amount of the fluctuation amounts obtained after the measuring operation has been commenced, there is such a merit that the blood pressure abnormality can be detected in high precision in addition to the similar effect to that of the first embodiment.

(Fifth Embodiment)

In the case that blood pressure is gradually lowered, there are some cases that a fluctuation amount of low frequency components is gradually increased. In such a case, if the above comparison operation is carried out when the measuring operation is commenced similar to the fourth embodiment, then the following determination is performed. That is, it is so determined that the fluctuation amount is always and largely increased.

However, in such a case, since a patient and a medical staff member may conceive that measuring operation of blood pressure need not be frequently carried out, the occurrence of this problem can be avoided by such a manner that data to be compared are continuously updated in such a case.

Figure 14:
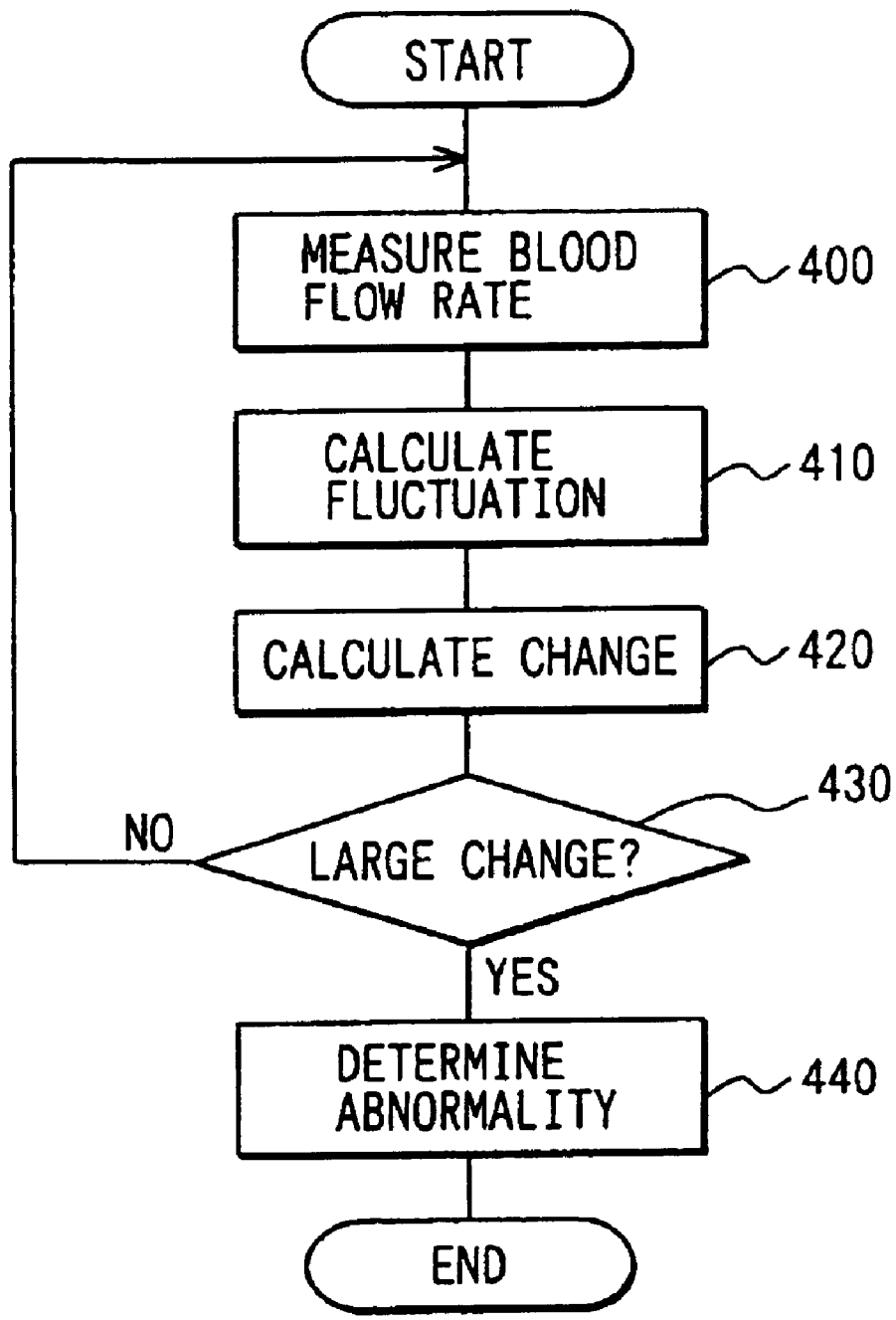
FIG. 14 is a flow diagram showing a process operation capable of detecting a blood pressure abnormality according to the fifth embodiment of the present invention.

FIG. 14 is a flow diagram for explaining the above process operations. At step 400, a blood flow rate is measured based upon a pulse wave signal. In the subsequent step 410, while the blood flow rate is measured, fluctuation amount of low frequency components is continuously calculated. At the next step 420, a calculation is made of such a change amount between an averaged value of fluctuation amounts of low frequency components, which were acquired before certain constant time (for example, before several tens of seconds to several minutes), and a presently acquired fluctuation amount. For example, in the case that a change amount is calculated every time one minute has passed, such a difference is calculated, that is, the difference between an averaged value of fluctuation amounts for 1 minute during previous measurement and an averaged value of fluctuation amounts for 1 minute during present measurement.

At the next step 430, while the change amount of the fluctuation amount is continuously compared with a certain threshold value, in such a case that the change amount of the fluctuation amounts is smaller than the threshold value, the process operation returns to the previous step 440. On the other hand, when the change amount of the fluctuation amounts is larger than or equal to the threshold value, the data processing apparatus unit 5 determines that a clinical and physiological abnormality (blood pressure abnormality) is present.

In accordance with this embodiment, the similar effect to that of the first embodiment may be achieved. Also, in accordance with this embodiment, the data processing apparatus unit 5 determines that no blood pressure abnormality occurs as to such a blood pressure change that this blood pressure is gradually changed for several minutes up to several hours. Also, the data processing apparatus unit 5 determines that a blood pressure abnormality is present in such a case that this blood pressure is rapidly changed within several minutes. Therefore, in particular, this blood pressure monitoring apparatus provides such a superior merit when rapid blood pressure abnormalities are detected, while these blood pressure abnormalities may occur within several minutes.

In accordance with this embodiment, while the fluctuation amounts are continuously compared with such fluctuation amounts acquired before constant time (that is, sequentially changed), the change amount thereof is calculated, and also the fluctuation amount is updated by the new data. Alternatively, in such a case that the data processing apparatus unit 5 determines that the blood pressure abnormality is present based upon the change amount of the fluctuation amounts, such a fluctuation amount to be compared may not be updated by the new data but may be fixed. Then, this fixed fluctuation amount may be continuously compared with such a fluctuation amount to be compared. As a result, the blood pressure abnormality can be properly detected.

(Sixth Embodiment)

The above threshold value may be previously set, while this threshold value is used to instruct the blood pressure measuring apparatus 9 to commence the measuring operation of blood pressure when it is so confirmed that a fluctuation amount of low frequency components is increased. For instance, in such a case of FIGS. 4A and 4B, as the threshold value for starting the blood pressure measurement, if this value is set 5 times large than a fluctuation amount of low frequency components when the measuring operation is commenced, then it is possible to grasp whether blood pressure is lowered.

However, this threshold value may be changed, depending upon individual patients, and physical conditions of a patient. Therefore, in accordance with this fifth embodiment, when the measurement of the blood pressure is commenced, this threshold value is arbitrarily set.

As a consequence, the similar effect to that of the first embodiment may be achieved, and also, the blood pressure abnormality can be correctly detected in response to the conditions of the patients.

(Seventh Embodiment)

In accordance with this seventh embodiment, the threshold value used in the blood pressure measuring operation in the sixth embodiment (that is, threshold value used to issue instruction of starting blood pressure measurement) is changed based upon both a blood pressure value measured in the blood pressure measuring apparatus unit 9, and also, a fluctuation amount of low frequency components acquired when the blood pressure is measured.

Figure 15:
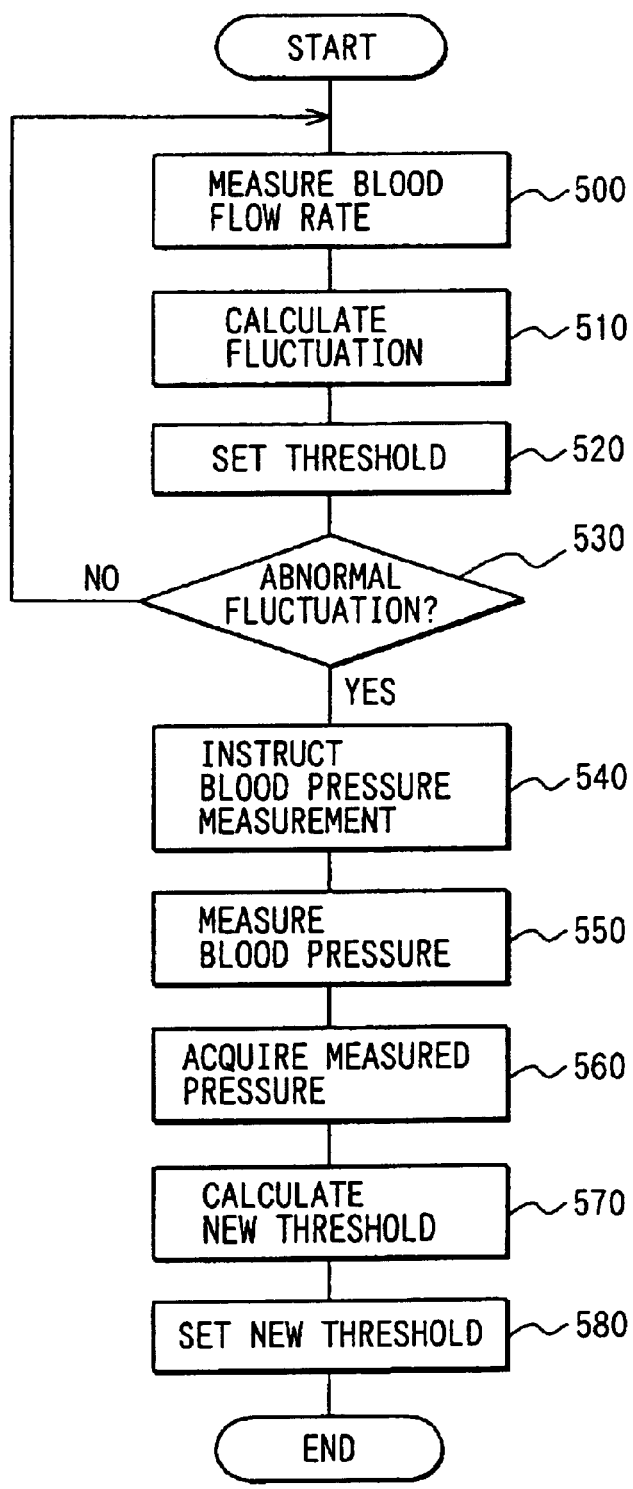
FIG. 15 is a flow diagram showing a process operation capable of detecting a blood pressure abnormality according to the seventh embodiment of the present invention.

FIG. 15 is a flow diagram for explaining process operations of this blood pressure monitoring apparatus. At the first step 500, a blood flow rate is measured based upon a pulse wave signal. At the subsequent step 510, a fluctuation amount of low frequency components is calculated.

At the next step 520, when the measurement is commenced, such a threshold value used to determine an abnormality (threshold value of change amount of fluctuation amounts) is firstly set by considering a patient and physical conditions of this patient on the day of this measurement. For example, such a threshold value is set, which is several times larger than that used when the measurement is commenced.

At the next step 530, the data processing apparatus unit 5 determines whether a change amount of the calculated fluctuation amounts is abnormal (larger than or equal to the threshold value). When this change amount is smaller than the threshold value, that is, normal condition, the process operation returns to the previous step 500. On the other hand, when this change amount is larger than or equal to the threshold value, the process operation advances to step 540 in which the data processing apparatus unit 5 instructs the measurement of the blood pressure.

At step 550, blood pressure is actually measured. At the subsequent step 560, the measured blood pressure value is acquired. At the next step 570, a new threshold value is calculated based upon the acquired value (abnormality determination threshold value).

At the next step 580, the threshold value is again set. For example, in such a case that the blood pressure value is sufficiently stable, the preset threshold value is set to a higher threshold value. As a result, such cumbersome operation that the blood pressure measurement is frequently carried out may be reduced. Also, when it is predictable that the blood pressure value is lowered and therefore the abnormality is expected, the preset threshold value is set to a lower threshold value. As a consequence, the occurrence of such an abnormality can be sensed at more proper timing.

In accordance with this embodiment, the blood pressure abnormality can be sensed in more precise manners in addition to the similar effect to that of the first embodiment. Since this threshold value can be again set during the actual measuring operation, the precision can be continuously improved. While the threshold value may be again set in an automatic manner, this threshold value may be again set in a manual manner.

(Eighth Embodiment)

In this eighth embodiment, a change contained in blood flow rates measured by the skin blood flow rate detecting apparatus unit 7 is outputted on, for instance, the display of the output unit 15. As a result, while a medical staff member and the like observes this change of the blood flow rates, such a threshold value used to detect a blood pressure abnormality as explained in the seventh embodiment may be changed.

Also, since the measuring operation of such a blood flow rate is repeatedly carried out several times, the threshold value may be set in a more proper manner. This setting operation of the threshold value may be carried out in either a manual manner or a software analysis manner. As a consequence, the threshold value of starting the blood pressure measuring operation can be set in a more proper manner.

(Ninth Embodiment)

In the first embodiment, the blood pressure monitoring apparatus equipped with the skin blood flow rate detecting apparatus 7, the blood pressure measuring apparatus unit 9, the alarm issuing unit 13, and the like has been exemplified. In this ninth embodiment, while the blood pressure monitoring apparatus is arranged by the skin blood flow rate detecting unit 7 and the alarm issuing unit 13, blood pressure may be measured by employing a hemomanometer belonging to another apparatus, or by a medical staff member.

As a method for issuing an alarm, a display lamp may be turned on and/or alarm sound may be produced. Also, in the case that a central management is carried out in a medical field and the like, an alarm command may be notified to a centralized management room. Furthermore, since an alarm command is applied to a portable telephone and/or electronic appliances (for example, television and radio) owned by a third party, a proper medical treatment may be carried out.

(Tenth Embodiment)

Figure 16:
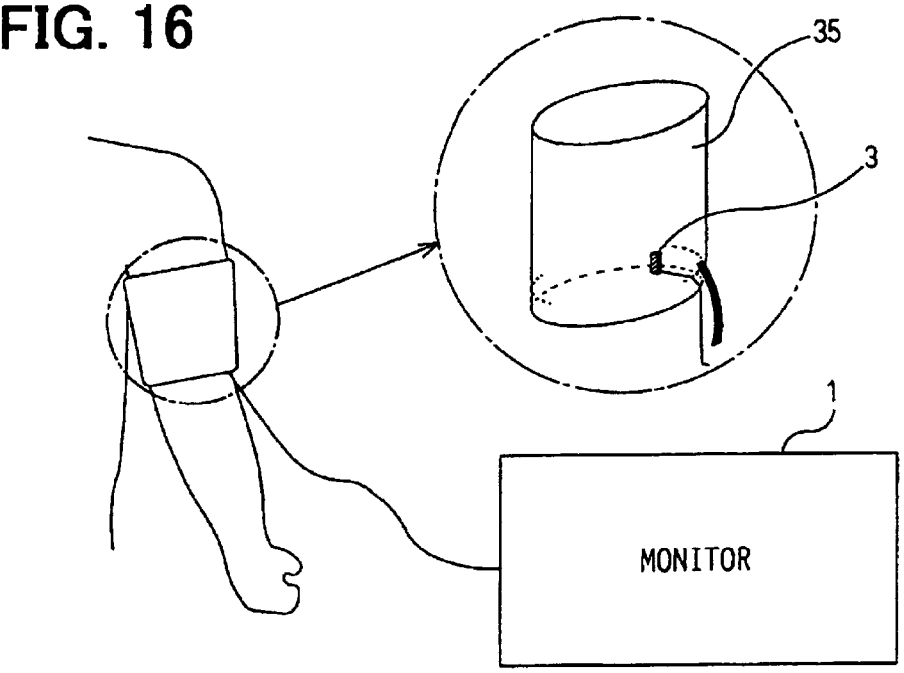
FIG. 16 is a schematic view showing a conceptual structure of a blood pressure monitoring apparatus according to the tenth embodiment of the present invention.

In the tenth embodiment, as represented in FIG. 16, the pulse wave sensor 3 is mounted on the cuff 35.

As a result, since the mounting articles to a patient can be grouped as one mounting article, cumbersome works of these mounting articles can be reduced. In this case, the cuff 35 is preferably mounted on such a pulse where when pressure is applied to the cuff 35, the applied pressure can be hardly give an adverse influence.

(Eleventh Embodiment)

In this embodiment, as shown in FIG. 1, while a change contained in blood flow rates, which is caused by body motion, is acquired by the body motion detecting apparatus unit (body motion sensor) 17, the adverse influence caused by this body motion is eliminated, so that an erroneous determination of a blood pressure abnormality can be reduced.

Figure 17:
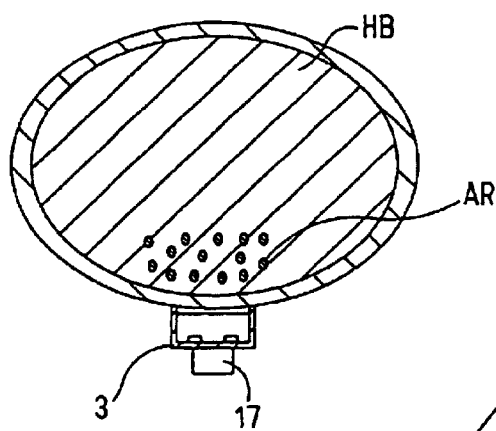
FIG. 17 is a schematic view showing a portion of a blood pressure monitoring apparatus according to the eleventh embodiment of the present invention.

As the body motion sensor 17, an acceleration sensor, an optical sensor, a resistance measurement sensor, and the like may be employed. Alternatively, as illustrated in FIG. 17, this body motion sensor 17 may be combined with the pulse wave sensor 3 in an integrated manner.

Figure 18:
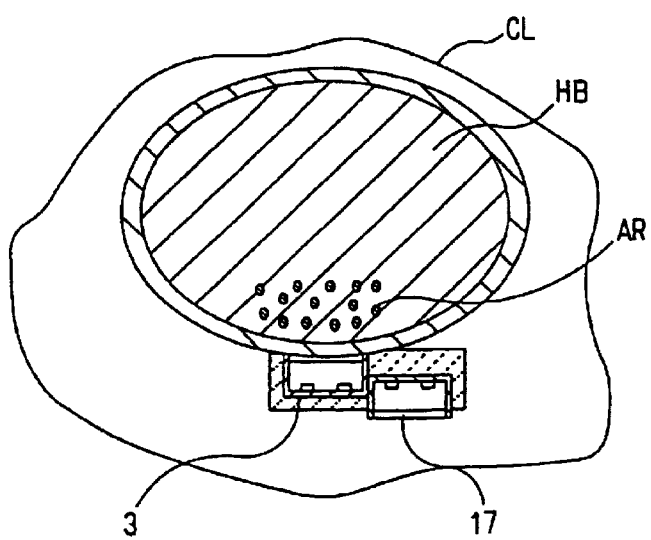
FIG. 18 is a schematic view showing another application example of the blood pressure monitoring apparatus of the eleventh embodiment.

Furthermore, the pulse wave sensor 3 may be utilized as the body motion sensor 17. For example, as shown in FIG. 18, the body motion sensor 17 having a similar construction as that of the pulse wave sensor 3 is mounted along a direction other than a skin. That is, when cloth CL is moved by body motion, an amount of reflection light from the cloth is changed, a variation of sensor outputs can be observed. Even when no cloth is worn, the direction of the body motion sensor 17 is changed by the body motion, so that an amount of light entering from an external environment is changed, and thus, body motion can be detected.

(Twelfth Embodiment)

This embodiment exemplifies such a method capable of reducing an erroneous determination caused by body motion noise by utilizing a sensor output of the body motion sensor 17.

Figure 19:
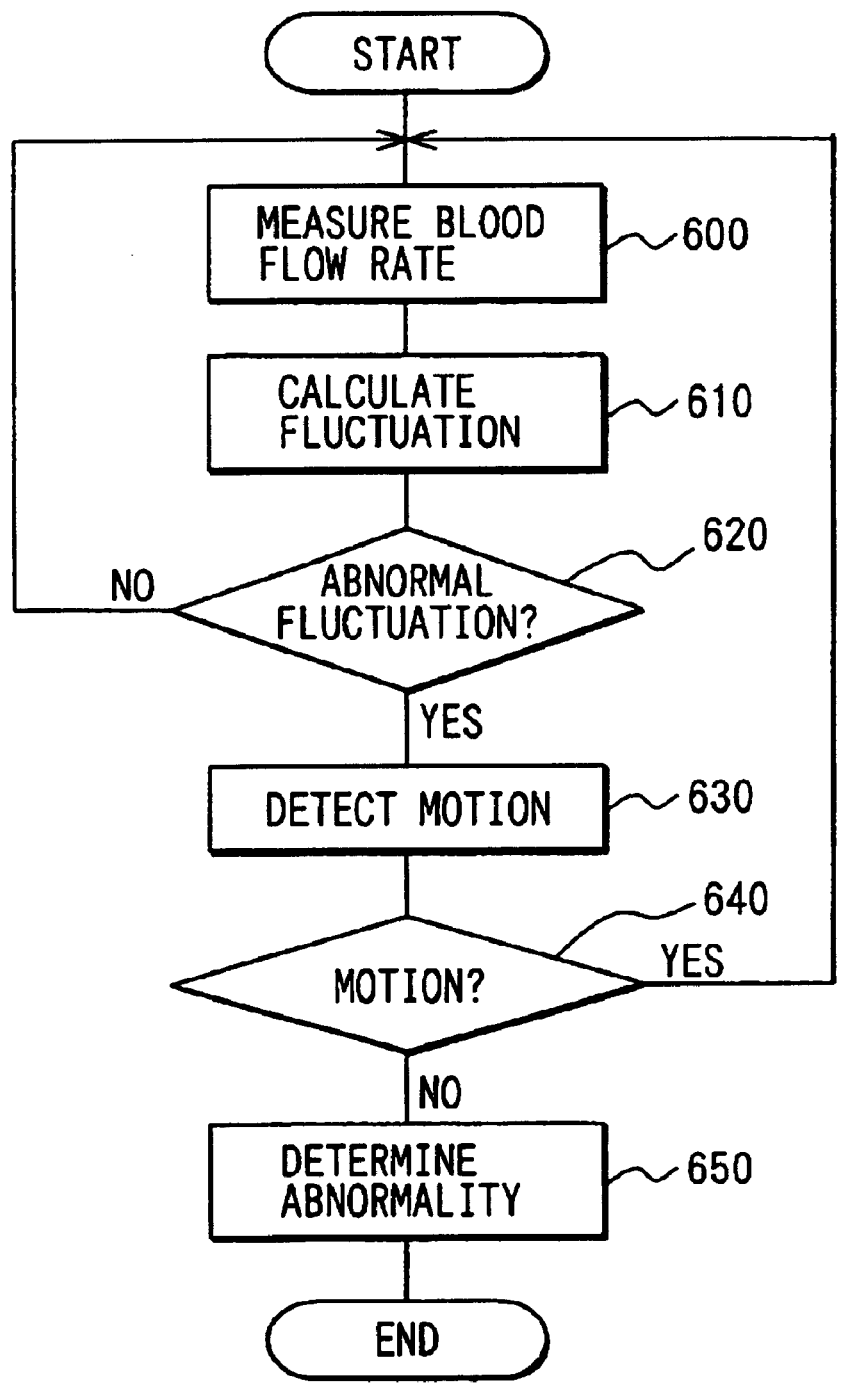
FIG. 19 is a flow diagram showing a process operation capable of detecting a blood pressure abnormality according to the twelfth embodiment of the present invention.

FIG. 19 is a flow diagram for explaining process operations of this blood pressure monitoring apparatus. At the first step 600, a blood flow rate is measured based upon a pulse wave signal. At the subsequent step 610, a fluctuation amount of low frequency components is calculated. At the next step 620, the data processing apparatus unit 5 determines whether a blood pressure abnormality is present based upon the calculated fluctuation amount of the low frequency components. When the data processing apparatus unit 5 determines certain possibilities of such a blood pressure abnormality, the process operation advances to step 630. On the other hand, when the data processing apparatus unit 5 determines that no blood pressure abnormality occurs, the process operation returns to step 600.

At step 630, body motion detection is carried out based upon a sensor output of the body motion sensor 17. At step 640, a determination of the body motion is carried out. When the data processing apparatus unit 5 determines that the body motion is detectable at this step, the process operation returns to the above step 600. On the other hand, when the data processing apparatus unit 5 determines that no body motion is detectable, the process operation advances to step 650.

At this step 650, the data processing apparatus unit 5 determines that the blood pressure abnormality is present, and thus, executes a process operation for issuing an alarm.

As a result, the blood pressure monitoring apparatus of this embodiment can determine the blood pressure abnormality in higher precision. That is, since the measurement value obtained by the pulse wave sensor 3 changes when the pulse wave sensor 3 is moved, in such a case that noise of frequency components is produced during this measuring operation, this determination can be very hardly carried out, while these frequency components of the noise correspond to a fluctuation amount of lower frequency components (which are employed as threshold reference of clinical and physiological abnormality). Under such a circumstance, in this embodiment, the body motion is continuously detected by using the body motion sensor 17 during the measuring operation. Then, in such a case that the data processing apparatus unit 5 determines that the blood pressure abnormality is present based upon the fluctuation amount, the data processing apparatus unit 5 determines whether there is an adverse influence caused by the body motion, so that the adverse influence caused by the body motion noise can be reduced.

It should be understood that the determination reference used to check whether the body motion is detectable may be changed during the measurement operation. That is, in the case that the body motion is very small, even when the sensor output of the body motion is small, there is such a need that presence of such a body motion should be determined. Thus, this threshold value for determining the presence of such a body motion is required to be set to a proper value. This setting operation may be carried out in a manual manner, or a software analysis manner.

(Thirteen Embodiment)

In a case that lowering of blood pressure is monitored as a blood pressure abnormality, an upper limit value of cuff pressure is set in order to reduce a load given to a person under measurement. Then, when blood pressure is higher than or equal to a certain value, the blood pressure measuring operation need not be carried out. That is, a blood pressure value of a patient is substantially constant under normal condition.

Therefore, in accordance with this thirteen embodiment, in such a case that the blood pressure of the patient is low under normal condition, the upper limit value of the cuff pressure is set to such a cuff pressure capable of measuring this blood pressure value. As a consequence, the load given to the person under measurement can be reduced.

(Fourteenth Embodiment)

The setting operation of the cuff pressure by the blood pressure measuring apparatus unit (hemomanometer) 9 shown in the thirteenth embodiment is changed in response to the condition of the patient. As a consequence, in this fourteenth embodiment, the cuff pressure is automatically set based upon a blood pressure value under measuring operation.

Figure 20:
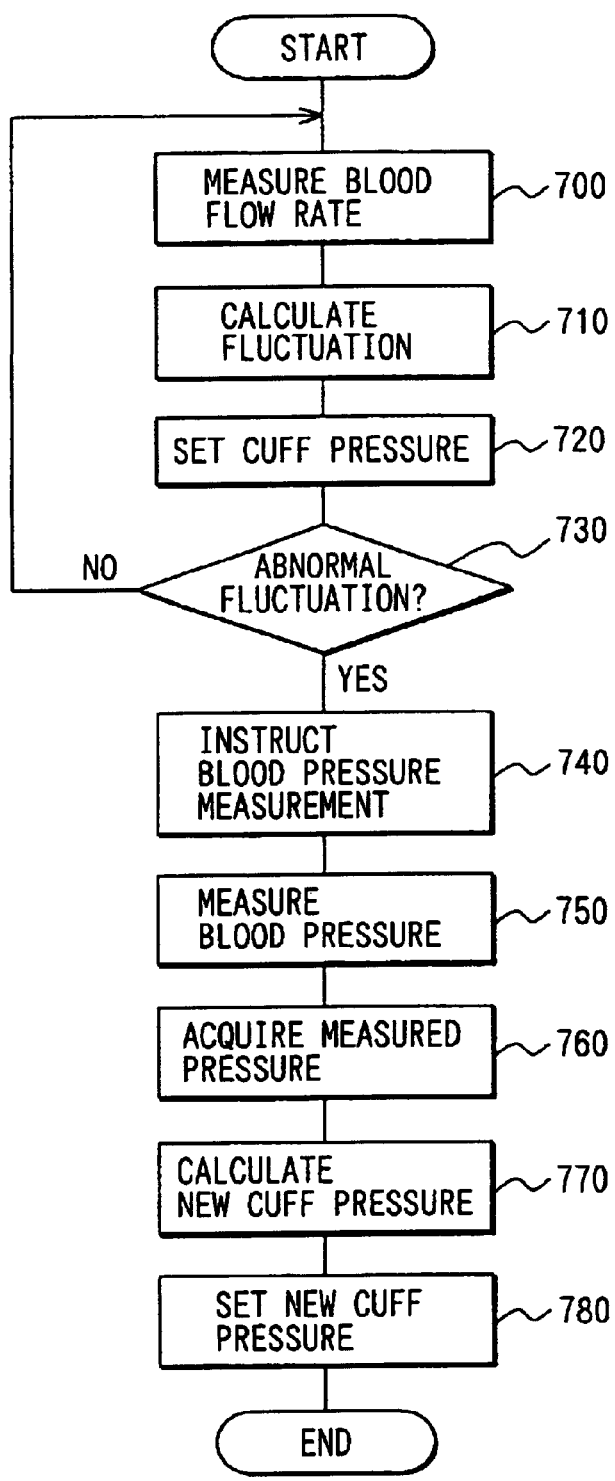
FIG. 20 is a flow diagram showing a process operation capable of detecting a blood pressure abnormality according to the fourteenth embodiment of the present invention.

FIG. 20 is a flow diagram for explaining process operations of the above automatic cuff pressure setting operation. First, at step 700, a blood flow rate is measured based upon a pulse wave signal. At the subsequent step 710, a fluctuation amount of low frequency components is calculated. At the next step 720, cuff pressure of a hemomanometer is set by considering a patient and a physical condition of the patient on this day.

At the next step 730, the data processing apparatus unit 5 determines whether a blood pressure abnormality is present based upon the calculated fluctuation amount of the low frequency components. When the data processing apparatus unit 5 determines that no blood pressure abnormality occurs, the process operation returns to the previous step 700. When the data processing apparatus unit 5 determines certain possibilities of such a blood pressure abnormality, the process operation advances to step 740.

At step 740, a blood pressure measurement is carried out. At the next step 750, blood pressure is actually measured. At the subsequent step 760, the measured blood pressure value is acquired. At the next step 770, a new cuff pressure is again calculated in response to the acquired blood pressure value. At step 780, the new cuff pressure is again set. For instance, in such a case that the blood pressure of the patient becomes relatively low, the cuff pressure is decreased. When the blood pressure becomes relatively high, the cuff pressure is increased. As a consequence, the load given to the patient can be reduced.

(Fifteenth Embodiment)

The blood pressure monitoring apparatus according to this embodiment predicts and senses a blood pressure abnormality by employing a plurality of pulse wave sensors 3.

For example, the plural sets of pulse wave sensors 3 are mounted on an arm within a range larger than or equal to 5 $mm^2$. Then, while pulse wave signals derived from the respective pulse wave sensors 3 are entered into the data processing apparatus unit 5, this data processing apparatus unit 5 predicts and senses a blood pressure abnormality by utilizing all of these pulse wave signals, or arbitrarily-selected numbers of pulse wave signals.

For example, in such a case that the blood pressure abnormality is determined by employing the pulse wave signals derived from three sets of these pulse wave sensors 3, only when the data processing apparatus unit 5 determines that an abnormality is present based upon more than two pulse wave signals, this data processing apparatus unit 5 determines that a blood pressure abnormality is present. Otherwise, the present condition is brought into such a condition just before this blood pressure abnormality is present. As a consequence, the determination precision of the blood pressure abnormality can be improved.

That is, since the blood pressure monitoring apparatus can confirm that the change in the fluctuation amounts of the low frequency components of the blood flow rates occur in a wider range of a human body, the prediction of the blood pressure abnormality can be correctly determined.

It should also be noted that the present invention is not limited to the above embodiments, but may be realized by various embodiment modes without departing from the technical scope and spirit of the present invention.

For instance, the present invention may be applied to a program used to execute a process operation in accordance with the above algorithm, and also may be applied to a recording medium for recording thereon this program. As this recording medium, various sorts of recording media may be employed, that is, an electronic control apparatus constituted as a microcomputer, a microchip, a flexible disk, a hard disk, and an optical disk. That is, if any recording media may record thereon the program capable of executing the above process operation of the blood pressure monitoring apparatus, then no specific limitation is made. It should also be understood that the above program is not merely limited to such a program stored in the above recording medium, but may be applied to such a program which is transmitted/received via a communication line such as the Internet.

Also, the above blood pressure monitoring apparatus may be applied to other cases. That is, a pulse wave signal acquired from a pulse wave sensor may be directly entered into such a data processing apparatus installed at just near the original place. Furthermore, for instance, while the data obtained from the pulse wave sensor is entered into such an apparatus as a personal computer, this acquired data may be transmitted to another data processing apparatus located at a remote place by using, for instance, the Internet so as to predict/sense a blood pressure abnormality, or to measure blood pressure.

While threshold values are set in a predetermined frequency range, for instance, both a frequency range indicative of a pulse wave and another frequency range representative of a fluctuation contained in pulse wave signals, either one or a plurality of peak values which exceed these threshold values may be employed as the peak value used to employ the above threshold of the blood pressure abnormality. The peak values correspond to, for example, average values MC and MA of the peak values in both the frequency ranges.

As a consequence, in this case, while a ratio MC/MA as to the average values of both these frequency ranges is employed, for example, the blood abnormality may be predicted/sensed.

Alternatively, for example, both in the frequency components of the frequency range indicative of the pulse waves, and in the frequency components of the frequency range representative of the fluctuation of the pulse wave signals, an integration value SC and another integration value SA of the respective frequency components in these frequency ranges are calculated. Then, while the peak values used to determine the blood pressure abnormality are substituted by these integration values, the threshold of the blood pressure abnormality may be carried out.

As a consequence, in this case, while a ratio SC/SA of these integration values of both the frequency ranges is employed, the blood pressure abnormality may be predicted/sensed.

Blood volume or blood flow speed may be alternatively used as a parameter indicating a blood flow condition in place of the blood flow rate used in the above embodiments.

What is claimed is:

1. A clinical and physiological abnormality monitoring apparatus comprising:
   means for detectiong vasomotion of a body in a percutaneous manner; and
   means for determining a clinical and physiological abnormality upon the detected vasomotion,
   wherein the detecting means detects a change contained in a blood flow condition of the blood vessels in the percutaneous manner so as to acquire a fluctuation of the blood flow condition caused by the vasomotion, the acquired fluctuation being used to determine the clinical and physiological abnormality.

2. A clinical and physiological abnormality monitoring apparatus as in claim 1, wherein:
   the detecting means detects frequency component corresponding to the fluctuation of the blood flow condition, which is lower than a frequency component corresponding to a pulse interval.

3. A clinical and physiological abnormality monitoring apparatus as in claim 1, wherein:
   the detecting means detects both frequency components corresponding to the pulse interval and corresponding to the fluctuation of the blood flow condition, which is lower than the frequency component corresponding to the pulse interval, the detected frequency components being used to determine the clinical and physiological abnormality.

4. A clinical and physiological abnormality monitoring apparatus as in claim 1, wherein:
   the detecting means detects a change contained in fluctuations of the blood flow condition after the measuring operation is commenced, the detected change contained in the fluctuations being used to determine the clinical and physiological abnormality.

5. A clinical and physiological abnormality monitoring apparatus as in claim 1, wherein:
   the detecting means detects a change contained in fluctuations of the blood flow condition before a predetermined period is detected, the detected change being used to determine the clinical and physiological abnormality.

6. A clinical and physiological abnormality monitoring apparatus as in claim 1, wherein:
   the detecting means includes a blood flow condition detecting apparatus unit for acquiring the fluctuation of the blood flow condition.

7. A clinical and physiological abnormality monitoring apparatus as in claim 1, wherein:
   the determining means determines the clinical and physiological abnormality based upon both the fluctuation of the blood flow condition and body motion.

8. A clinical and physiological abnormality monitoring apparatus as in claim 7, wherein:
   the detecting means includes a blood flow condition detecting apparatus unit for detecting the fluctuation of the blood flow condition; and
   a body motion detecting apparatus unit for detecting the body motion.

9. A clinical and physiological abnormality monitoring apparatus as in claim 1, wherein:
   the detecting means acquires a C-frequency component corresponding to the fluctuation of the blood flow condition from a measured pulse wave signal, the acquired C-frequency component being used to determine the clinical and physiological abnormality.

10. A clinical and physiological abnormality monitoring apparatus as in claim 9, wherein:
    the C-frequency component of a predetermined frequency range corresponds to a frequency component indicative of the fluctuation of the pulse wave signals in which the pulse wave is continued.

11. A clinical and physiological abnormality monitoring apparatus as in claim 9, wherein:
    the C-frequency component of the predetermined frequency range corresponds to a frequency component lower than an A-frequency component of a frequency range corresponding to the respective pulse waves.

12. A clinical and physiological abnormality monitoring apparatus as in claim 11, wherein:
    the determining means compares the value C equivalent to the C-frequency component with a value A equivalent to the A-frequency component.

13. A clinical and physiological abnormality monitoring apparatus as in claim 12, wherein:
    the determining means determines the clinical and physiological abnormality based upon a ratio C/A of the value C equivalent to the C-frequency component with respect to the value A equivalent to the A-frequency component.

14. A clinical and physiological abnormality monitoring apparatus as in claim 12, wherein:
the determining means determines the clinical and physiological abnormality based upon a change amount of ratios C/A of the value C equivalent to the C-frequency component with respect to the value A equivalent to the A-frequency component.

15. A clinical and physiological abnormality monitoring apparatus as in claim 9, wherein:
the determining means compares a value C equivalent to the C-frequency component with a predetermined threshold value.

16. A clinical and physiological abnormality monitoring apparatus as in claim 9, wherein:
the detecting means acquires the C-frequency component in a frequency range lower than about 0.5 Hz.

17. A clinical and physiological abnormality monitoring apparatus as in claim 16, wherein:
the detecting means acquires the C-frequency component in a frequency range lower than about 0.25 Hz.

18. A clinical and physiological abnormality monitoring apparatus as in claim 9, wherein:
the detecting means employs, as the value C equivalent to the C-frequency component, a maximum peak value in the predetermined frequency range.

19. A clinical and physiological abnormality monitoring apparatus as in claim 9, wherein:
the detecting means employs, as the value C equivalent to the C-frequency component, a peak value which is larger than a threshold value in the predetermined frequency range.

20. A clinical and physiological abnormality monitoring apparatus as in claim 9, wherein:
the detecting means employs, as the value C equivalent to the C-frequency component, an integral value in the predetermined frequency range.

21. A clinical and physiological abnormality monitoring apparatus as in claim 9, wherein:
the detecting means includes a plurality of pulse wave sensors.

22. A clinical and physiological abnormality monitoring apparatus as in claim 21, wherein:
the detecting means employs pulse wave signals derived from the plurality of pulse wave sensors larger than a predetermined number.

23. A clinical and physiological abnormality monitoring apparatus as in claim 21, wherein:
the pulse waves are measured at a clinical and physiological area larger than about 5 mm 2 by using the pulse wave sensor.

24. A clinical and physiological abnormality monitoring apparatus as in claim 1, further comprising:
notifying means for notifying the clinical and physiological abnormality.

25. A clinical and physiological abnormality monitoring apparatus as in claim 1, wherein:
the clinical and physiological abnormality corresponds to a blood pressure abnormality of the body.

26. A blood pressure monitoring apparatus comprising:
means for detecting vasomotion of a body in a percutaneous manner; and
means for measuring a blood pressure based upon the detected vasomotion,
wherein the detecting means detects a change contained in a blood flow condition of the blood vessel in the percutaneous manner so as to acquire a fluctuation of the blood flow condition caused by the vasomotion, the acquired fluctuation being used to measure the blood pressure.

27. A blood pressure monitoring apparatus as in claim 26, wherein:
the detecting means detects a frequency component corresponding to the fluctuation of the blood flow condition, which is lower than a frequency component corresponding to a pulse interval, the detected frequency component being used to measure the blood pressure.

28. A blood pressure monitoring apparatus as in claim 26, wherein:
the detecting means detects both frequency components corresponding to the pulse interval and corresponding to the fluctuation of the blood flow condition, which is lower than the frequency component corresponding to the pulse interval, the detected both frequency components being used to measure the blood pressure.

29. A blood pressure monitoring apparatus as in claim 28, wherein:
the measuring means measures the blood pressure based upon a ratio of a frequency component equivalent to a pulse interval with respect to a frequency component equivalent to the fluctuation of the blood flow condition, which is lower than the frequency component.

30. A blood pressure monitoring apparatus as in claim 26, wherein:
the detecting means detects a change contained in fluctuations of the blood flow condition after a measuring operation is commenced, the detected change contained in the fluctuations being used to measure the blood pressure.

31. A blood pressure monitoring apparatus as in claim 26, wherein:
the detecting means detects a change contained in fluctuations of the blood flow condition before a predetermined period, the detected change contained in the fluctuations being used to measure the blood pressure.

32. A blood pressure monitoring apparatus as in claim 26, wherein:
the detecting means variably sets a threshold value used to execute the blood pressure measurement.

33. A blood pressure monitoring apparatus as in claim 26, wherein:
the detecting means automatically adjusts a threshold value used to execute the blood pressure measurement based upon a blood pressure value which has already been measured.

34. A blood pressure monitoring apparatus as in claim 26, wherein:
a condition for the blood pressure measurement is set based upon both the fluctuation of the blood flow condition and body motion.

35. A blood pressure monitoring apparatus as in claim 26, wherein:
a change contained in the blood flow condition, an analysis result thereof, and the measured blood pressure value are externally outputted.

36. A blood pressure monitoring apparatus as in claim 26, further comprising:
the detecting means includes a blood flow condition detecting apparatus unit for acquiring the fluctuation of the blood flow condition.

37. A blood pressure monitoring apparatus as in claim 26, wherein:

the measuring means includes a blood pressure measuring apparatus unit for performing the blood pressure measurement.

38. A blood pressure monitoring apparatus as in claim 37, wherein:

the blood pressure measuring apparatus unit has a cuff.

39. A blood pressure monitoring apparatus as in claim 38, wherein:

a cuff-pressure applying amount of the blood pressure measuring apparatus unit used when a subsequent blood pressure measurement is carried out is automatically adjusted based upon the measured blood pressure value.

40. A blood pressure monitoring apparatus as in claim 26, wherein:

the detecting means includes a blood flow condition detecting apparatus unit for acquiring the fluctuation of the blood flow condition; and the measuring means includes a blood pressure measuring apparatus unit for performing the blood pressure measurement.

41. A blood pressure monitoring apparatus as in claim 40, further comprising:

an alarm issuing unit for issuing an alarm in the case that an abnormality of the blood pressure is detected.

42. A blood pressure monitoring apparatus as in claim 26, wherein:

the detecting means includes a blood flow condition detecting apparatus unit for acquiring the fluctuation of the blood flow condition; and the measuring means includes an alarm issuing unit for issuing an alarm in the case that an abnormality of the blood pressure is detected.

43. A blood pressure monitoring apparatus as in claim 26, wherein:

the detecting means includes a blood flow condition detecting apparatus unit for detecting the fluctuation of the blood flow condition, and a body motion detecting apparatus unit for detecting the body motion.

44. A blood pressure monitoring apparatus as in claim 26, wherein:

the detecting means includes a plurality of detecting units for detecting the change contained in the blood flow condition.

45. A blood pressure monitoring apparatus as in claim 26, wherein:

the measuring means stops measuring a blood pressure value higher than a predetermined upper-limit blood pressure.

* * * * *